(12) United States Patent
Takeda

(10) Patent No.: US 9,536,501 B2
(45) Date of Patent: Jan. 3, 2017

(54) RADIOGRAPHIC-IMAGE PROCESSING DEVICE

(71) Applicant: KONICA MINOLTA, INC., Chiyoda-ku, Tokyo (JP)

(72) Inventor: Yoshihiro Takeda, Hachioji (JP)

(73) Assignee: KONICA MINOLTA, INC., Tokyo (JP)

(*) Notice: Subject to any disclaimer, the term of this patent is extended or adjusted under 35 U.S.C. 154(b) by 25 days.

(21) Appl. No.: 14/092,572

(22) Filed: Nov. 27, 2013

(65) Prior Publication Data

US 2014/0168276 A1 Jun. 19, 2014

(30) Foreign Application Priority Data

Dec. 13, 2012 (JP) ................................ 2012-272086

(51) Int. Cl.
*G09G 5/373* (2006.01)
*A61B 6/00* (2006.01)
(52) U.S. Cl.
CPC .............. *G09G 5/373* (2013.01); *A61B 6/463*
(2013.01); *A61B 6/465* (2013.01); *A61B 6/52*
(2013.01); *A61B 6/469* (2013.01); *G09G 2340/045* (2013.01); *G09G 2380/08* (2013.01)
(58) Field of Classification Search
CPC ....... A61B 19/5244; A61B 5/055; A61B 8/00; A61B 6/032; A61B 6/08; A61B 6/502; A61B 6/463; A61B 6/465; A61B 6/52; A61B 6/469; G01N 23/04; H04N 5/32; G06T 7/0004; G96K 9/00; G09G 5/373; G09G 2340/045; G09G 2380/08
USPC ........ 345/671, 418, 629; 600/407, 410, 437; 378/4, 62, 63, 19, 98.2, 37
See application file for complete search history.

(56) References Cited

U.S. PATENT DOCUMENTS

| | | | | |
|---|---|---|---|---|
| 5,883,933 A | * | 3/1999 | Goto et al. | 378/4 |
| 6,243,485 B1 | * | 6/2001 | Murakami | G06T 7/0012 |
| | | | | 382/132 |
| 8,238,633 B2 | | 8/2012 | Ida et al. | |
| 2001/0038707 A1 | * | 11/2001 | Ohara | A61B 6/4233 |
| | | | | 382/132 |
| 2004/0068170 A1 | * | 4/2004 | Wang et al. | 600/407 |
| 2008/0232668 A1 | * | 9/2008 | Kitamura | G06T 7/0081 |
| | | | | 382/132 |

(Continued)

FOREIGN PATENT DOCUMENTS

| | | |
|---|---|---|
| JP | 2005130928 A | 5/2005 |
| JP | 2012-071039 A | 4/2012 |

OTHER PUBLICATIONS

Japanese Office Action (and English translation thereof) dated Apr. 5, 2016, issued in counterpart Japanese Application No. 2012-272086.

*Primary Examiner* — Chante Harrison
(74) *Attorney, Agent, or Firm* — Holtz, Holtz & Volek PC

(57) ABSTRACT

A radiographic-image processing device executes image processing on radiographic image data obtained by radiographic imaging of a diagnostic target part as an imaging subject. The device includes a display unit and an enlargement display unit. The display unit displays a radiographic image based on the radiographic image data. The enlargement display unit enlarges a predetermined area including an interest area in the radiographic image and which displays the enlarged predetermined area on the display unit as an initial image which is the first to be displayed after radiographic imaging.

7 Claims, 20 Drawing Sheets

(56) References Cited

U.S. PATENT DOCUMENTS

| | | | |
|---|---|---|---|
| 2009/0060312 A1* | 3/2009 | Kitamura | G06T 5/50 |
| | | | 382/132 |
| 2010/0177865 A1* | 7/2010 | Yoshimura | 378/19 |
| 2011/0058653 A1* | 3/2011 | Baumgart et al. | 378/98.2 |
| 2012/0059239 A1* | 3/2012 | Yamaguchi | G06T 7/20 |
| | | | 600/407 |
| 2013/0121468 A1* | 5/2013 | Ohta et al. | 378/63 |
| 2013/0156154 A1* | 6/2013 | Watanabe | A61B 6/022 |
| | | | 378/42 |
| 2014/0103222 A1* | 4/2014 | Ohta | A61B 6/025 |
| | | | 250/393 |
| 2015/0071406 A1* | 3/2015 | Temmei | A61B 6/469 |
| | | | 382/132 |

* cited by examiner

FIG.3

| RECORD NO. | UID | IMAGING DATE AND TIME | EXAMINATION ID | EXAMINATION PART | PATIENT ID | ... | ORIGINAL IMAGE | INITIAL IMAGE | THUMBNAIL IMAGE |
|---|---|---|---|---|---|---|---|---|---|
| 1 | 0120080101 | 2008.01.01 01:00:01 | 1234 | ABDOMEN | 00001 | ... | C:¥XXX¥000¥... | C:¥XXX¥000¥... | C:¥XXX¥000¥... |
| 2 | 0120080101 | 2008.01.01 01:00:02 | 1234 | ABDOMEN | 00001 | ... | C:¥XXX¥000¥... | C:¥XXX¥000¥... | C:¥XXX¥000¥... |
| 3 | 0120080101 | 2008.01.01 01:00:03 | 1234 | ABDOMEN | 00001 | ... | C:¥XXX¥000¥... | C:¥XXX¥000¥... | C:¥XXX¥000¥... |
| 4 | 0120080101 | 2008.01.01 01:00:04 | 1234 | ABDOMEN | 00001 | ... | C:¥XXX¥000¥... | C:¥XXX¥000¥... | C:¥XXX¥000¥... |
| 5 | 0120080102 | 2008.01.02 11:55:31 | 1235 | CHEST (FRONT SIDE) | 00120 | ... | C:¥XXX¥△△△¥... | C:¥XXX¥△△△¥... | C:¥XXX¥△△△¥... |
| 6 | 0120080102 | 2008.06.09 14:00:00 | 28 | BLOOD, URINE | 00001 | ... | C:¥XXX¥○○○¥... | C:¥XXX¥○○○¥... | C:¥XXX¥△△△¥... |
| 7 | 0120080103 | 2008.06.09 15:00:00 | 29 | BLOOD | 00059 | ... | C:¥XXX¥○○△¥... | C:¥XXX¥○○△¥... | C:¥XXX¥○○△¥... |
| ... | ... | ... | ... | ... | ... | ... | ... | ... | ... |

331a

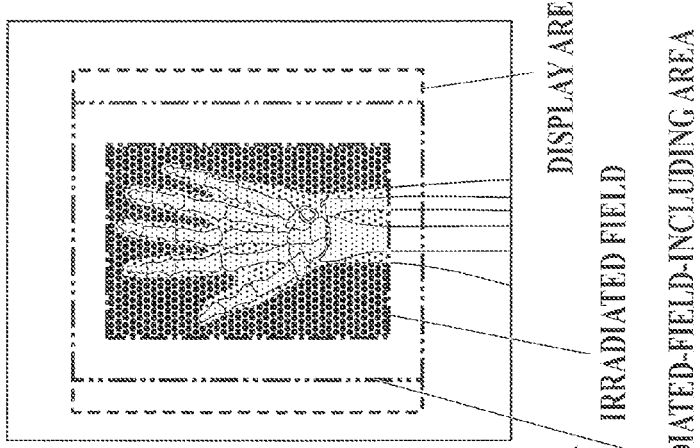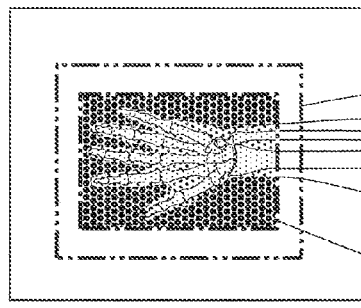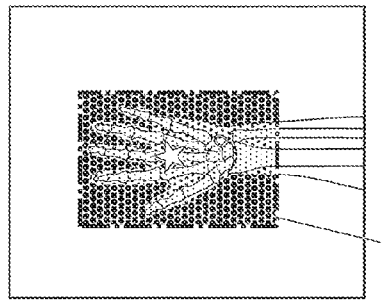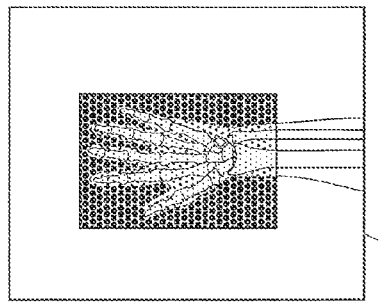

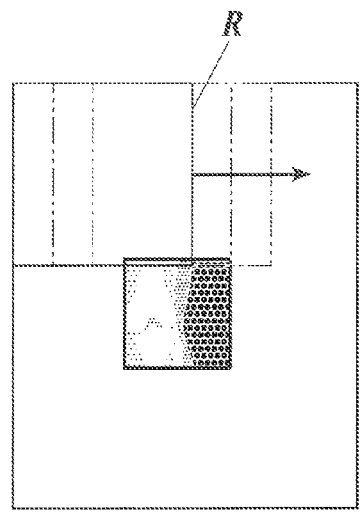
*FIG.10*
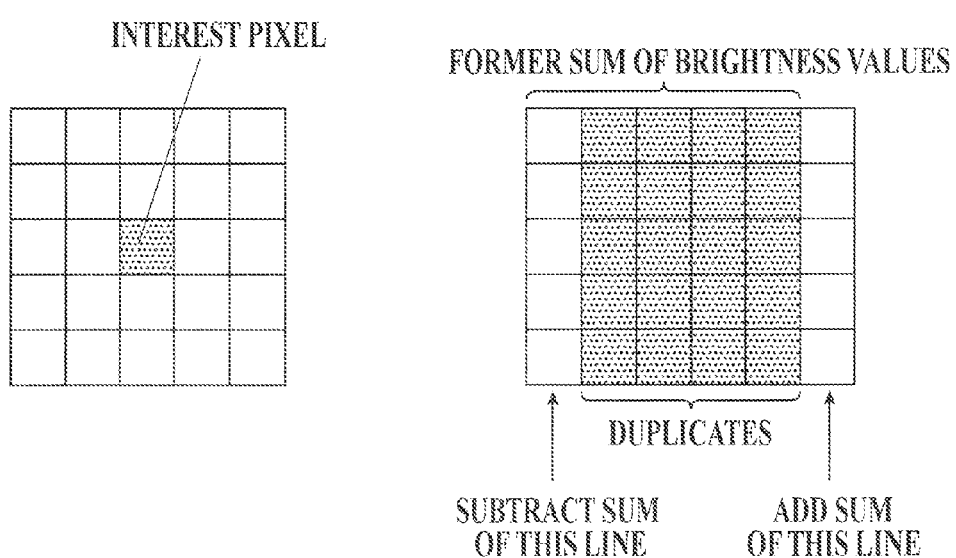
*FIG.11A*  *FIG.11B*

PROFILE OF MAXIMUM
VALUES WHEN SCANNED
IN HORIZONTAL DIRECTION

PROFILE OF MAXIMUM VALUES
WHEN SCANNED IN VERTICAL DIRECTION

FIG.15A
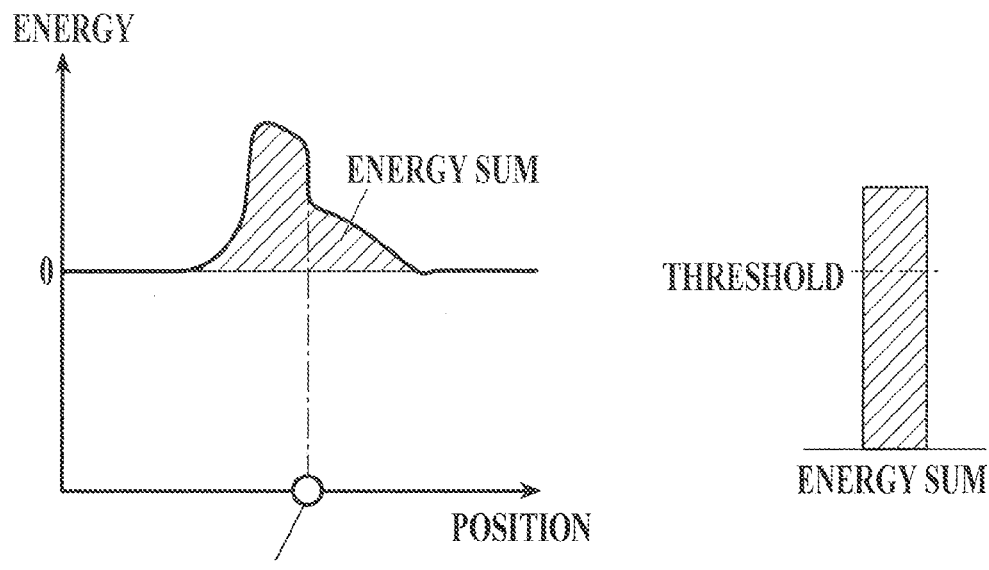
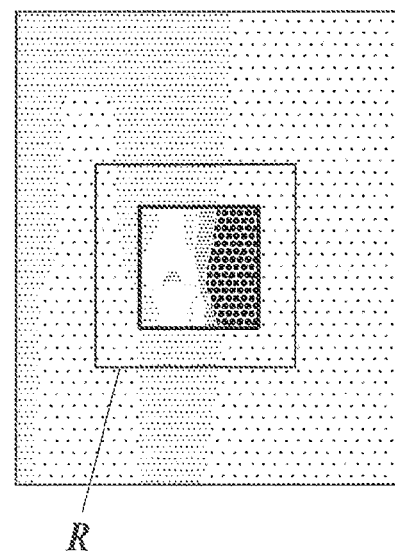

FIG.15B
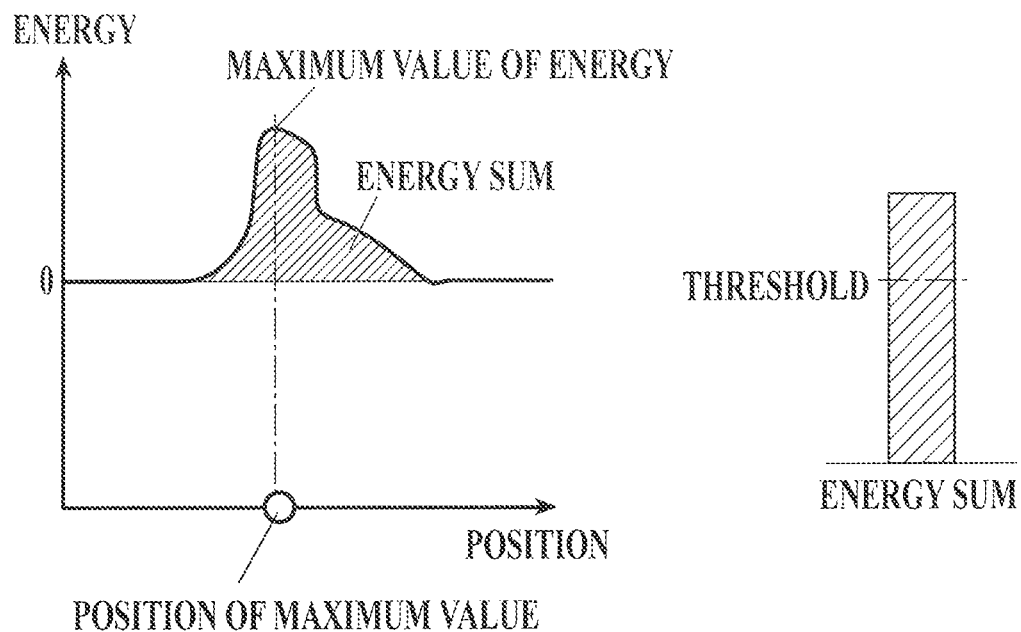
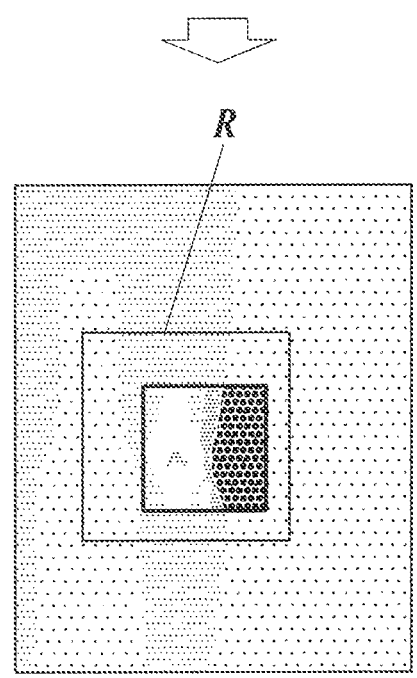

FIG.16
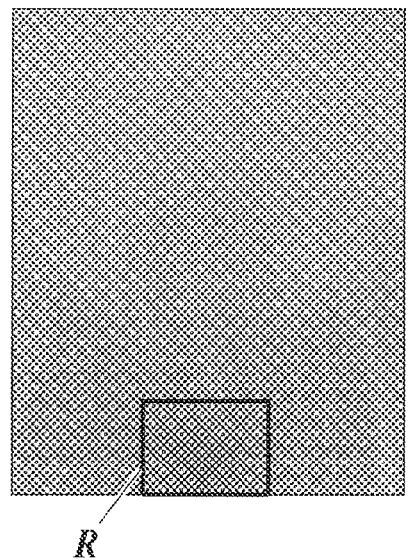
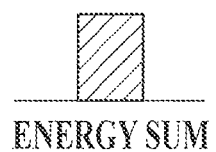
R
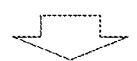
EXPAND
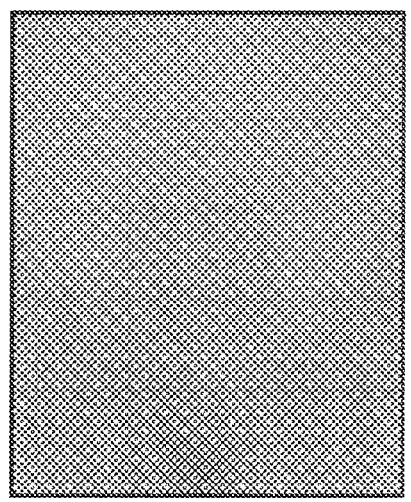

RADIOGRAPHIC-IMAGE PROCESSING DEVICE

BACKGROUND OF THE INVENTION

1. Field of the Invention

The present invention relates to a radiographic-image processing device.

2. Description of Related Art

Recently, in relatively small medical facilities, all diagnostic target parts have tended to be imaged by X-ray detector of one size, such as a large FPD (Flat Panel Detector).

However, if all diagnostic target parts are imaged by X-ray detector of one size, sometimes imaging is carried out on a diagnostic target part which is too small for the X-ray detector. In this case, sometimes a problem occurs as follows. Since the image size of a diagnostic target part is too small in relation to a size of the whole image, when the whole image is displayed on a display unit, areas other than the diagnostic target part cover most of the display unit. It is not appropriate for diagnosis.

There has been a known technique for displaying an image of an appropriate size on a display unit while diagnosis is made. In this technique, a radiographic image which is obtained by imaging a diagnostic target part is trimmed such that the unnecessary area is deleted from the radiographic image, and then the image is displayed on a display unit as the diagnostic image (See Japanese Patent Publication No. 2012-71039 for example).

However, the technique described in the above Japanese Patent Publication has a problem. In this technique, the area which is determined as unnecessary is deleted directly from the radiographic image which is obtained by imaging. Therefore, if a portion of an image included in the displayed diagnostic image does not meet one's intention, the original radiographic image must be read again and the scope for trimming must be designated again. It takes a lot of effort to adjust the scope of the diagnostic image.

SUMMARY OF THE INVENTION

It is an object of the present invention to solve the above problem. That is to provide a radiographic-image processing device that can easily adjust a scope of a diagnostic image.

In order to realize the above object, according to a first aspect of the present invention, there is provided a radiographic-image processing device which executes image processing on radiographic image data obtained by radiographic imaging of a diagnostic target part as an imaging subject, including:

a display unit which displays a radiographic image based on the radiographic image data; and an enlargement display unit which enlarges a predetermined area including an interest area in the radiographic image and which displays the enlarged predetermined area on the display unit as an initial image which is the first to be displayed after radiographic imaging.

Preferably, the radiographic-image processing device further includes a display-change unit which changes the initial image displayed on the display unit in accordance with operation by a user.

Preferably, the radiographic-image processing device further includes a recognition section which makes a user recognize that the initial image is an enlarged image of the predetermined area including the interest area in the radiographic image when the initial image is displayed on the display unit.

Preferably, in the radiographic-image processing device, the recognition section is an indicator displayed together with the initial image on the display unit when the initial image is displayed on the display unit, and the display-change unit changes the displayed initial image in accordance with operation on the indicator by a user.

Preferably, in the radiographic-image processing device, the recognition section is an indicator displayed on the display unit together with the initial image when the initial image is displayed on the display unit, and the display-change unit changes the displayed initial image in accordance with operation on the indicator by a user.

Preferably, in the radiographic-image processing device, the display-change unit switches between the initial image and a whole image obtained by radiographic imaging.

Preferably, in the radiographic-image processing device, the display-change unit moves the initial image or changes a display magnification of the initial image.

Preferably, in the radiographic-image processing device, the interest area is an irradiated-field area in the radiographic image.

Preferably, the radiographic-image processing device further includes a storage which stores a plurality of display information which defines a form and a size of an image to be displayed on the display unit, and the enlargement display unit selects display information from the plurality of display information stored in the storage on the basis of a form and a size of the interest area and sets a form and a size of the predetermined area.

Preferably, the radiographic-image processing device further includes a past-image storage which stores past-image data obtained in past radiographic imaging, and the enlargement display unit sets a form and a size of the predetermined area on the basis of the past-image data obtained for the same diagnostic target part of the same patient, which is stored in the past-image storage.

BRIEF DESCRIPTION OF THE DRAWINGS

The present invention will become more fully understood from the detailed description given hereinbelow and the appended drawings which are given byway of illustration only, and thus are not intended as a definition of the limits of the present invention, and wherein:

FIG. 3 shows an example of an image information table of an image database in FIG. 2;

FIG. 8A to FIG. 8D are schematic views illustrating the initial-image generation processing;

FIG. 10 shows an example wherein a rectangle is set on an original image;

FIG. 11A and FIG. 11B illustrate a preferable calculation method of an inside value;

FIG. 15A and FIG. 15B illustrate a method for setting a size and a position of the rectangle;

FIG. 16 illustrates a method for setting a size and a position of the rectangle when there is no area other than the irradiated field;

DETAILED DESCRIPTION OF THE PREFERRED EMBODIMENT

Hereinafter, an embodiment of the present invention will be described with reference to the drawings. Though various technical limitations which are preferable to perform the present invention are included in the after-mentioned embodiment, the scope of the invention is not limited to the following embodiment and the illustrated examples.

<Configuration of In-Facility System 1>

Figure 1:
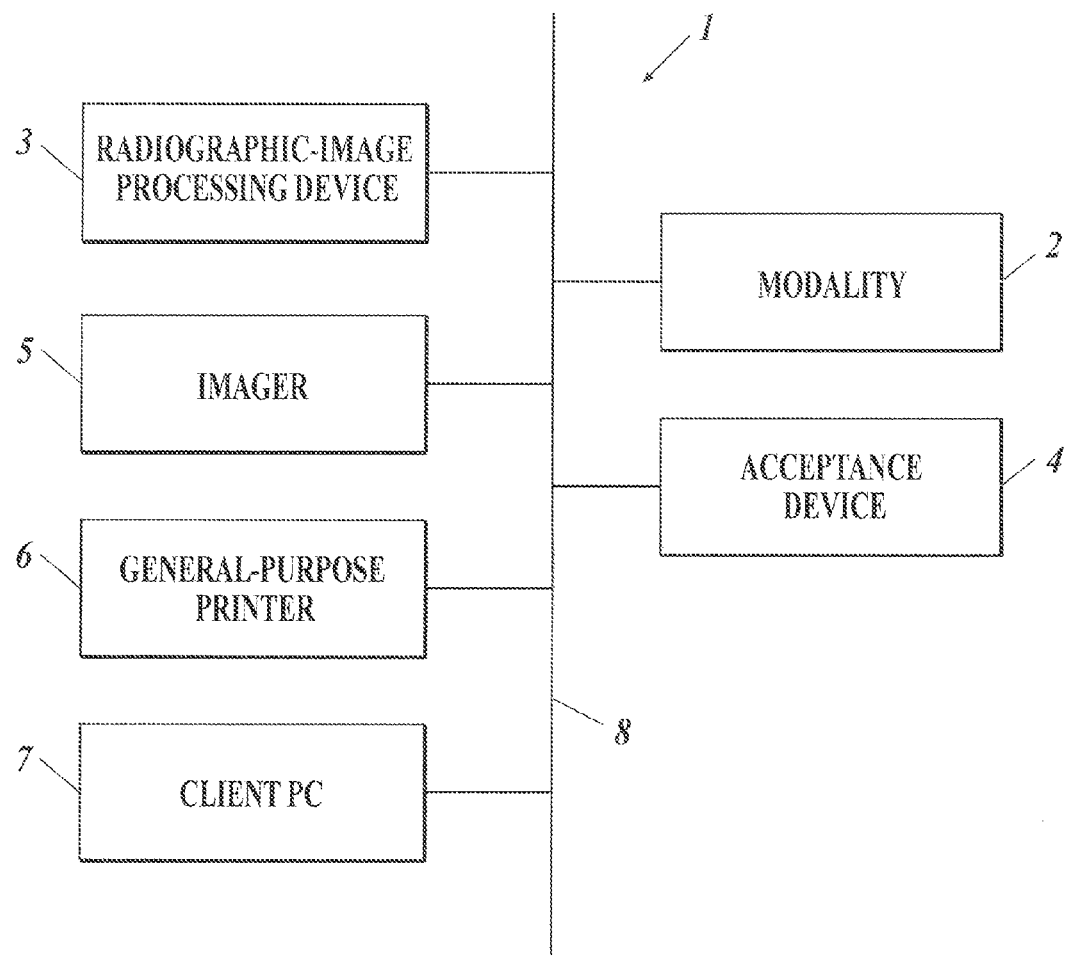
FIG. 1 is a block diagram showing a system configuration of an in-facility system according to an embodiment of the present invention.

FIG. 1 is a block diagram showing a system configuration of an in-facility system 1 to which a radiographic-image processing device 3 according to the embodiment is applied.

The in-facility system 1 is a small diagnostic system applied to relatively small medical facilities such as a medical practitioner's office or a clinic.

As shown in FIG. 1, the in-facility system 1 includes a modality 2, a radiographic-image processing device 3, an acceptance device 4, an imager 5, a general-purpose printer 6 and a client PC (Personal Computer) 7.

The devices constituting the in-facility system 1 are connected to a communication network (hereinafter referred to as just "network") 8, such as a LAN (Local Area Network), via a switching hub etc. for example, which is not shown in drawings.

The radiographic-image processing device 3 is preferably a WS (work station) in a medical-examination room wherein a doctor resides. It may be configured that the WS, which operates as the radiographic-image processing device 3, controls activation, processing condition, etc. of the modality.

DICOM (Digital Image and Communications in Medicine) standard is generally used as a communication method in a hospital. DICOM MWM (Modality Worklist Management) and DICOM MPPS (Modality Performed Procedure Step) are used for communication between devices that are connected to each other via LAN. In addition, other various communication methods are applicable to the embodiment.

<Configuration of Devices in In-Facility System 1>

Hereinafter, devices constituting the in-facility system 1 will be explained.

The modality 2 is an image generation device which obtains radiographic image, etc. by imaging a diagnostic target part of a patient as an imaging subject and which digitizes the image to generate digital data of a medical image, such as a radiographic image, etc. which is used for an X-ray interpretation, etc.

In this embodiment, the modality 2 is a DR (Digital Radiography) device consisting of an X-ray imaging device, a FPD (Flat Panel Detector), etc.

The FPD is an X-ray detector which converts energy of X-ray which has passed through a subject and used for irradiation into an electric signal to obtain an X-ray transmission image.

In this embodiment, the modality 2 has a function to attach image attribute information, such as a UID, an imaging date and time, an examination ID and an examination part, to each radiographic image in a format equivalent to the DICOM standard. That is to say, a radiographic image with these image attribute information attached thereto is input to the radiographic-image processing device 3 from the modality 2. The UID is a unique ID which specifies a radiographic image in the in-facility system 1.

The modality 2 has an input unit (not shown in drawings), such as a keyboard having character keys, numeral keys, etc., from which patient information for specifying a patient who is an imaging subject is input. The patient information widely includes information for specifying a patient, such as patient ID, patient name (kanji), patient name (kana), patient name (ASCII), gender, date of birth and age.

There is no need to input all of them to the modality 2. Information to be input can be only a part of patient information. The input section of the modality 2 can be, for example, a numeric keypad, etc. if the modality 2 is the one that requires only a patient ID as patient information.

The image attribute information and the patient information above are used as attachment information which is attached to the radiographic image generated in the modality 2. The modality 2 generates the radiographic image in a DICOM file format under the DICOM standard, and send the generated radiographic image to the radiographic-image processing device 3 via a network 8. This DICOM file consists of an image section and a header section. Image data of the radiographic image is written to the image section. The attachment information concerning the radiographic image is written to the header.

The radiographic-image processing device 3 is installed at a medical examination room for example.

The radiographic-image processing device 3 relates the radiographic image generated by the modality 2 to corresponding patient information and stores the radiographic image in a storage 33 by putting the radiographic image onto an image database 331. Also, the radiographic-image processing device 3 displays images, etc. when a doctor carries out an X-ray interpretation, etc. The radiographic-image processing device 3 may have a monitor (display unit) with higher definition than definition of a monitor of a common PC.

Figure 2:
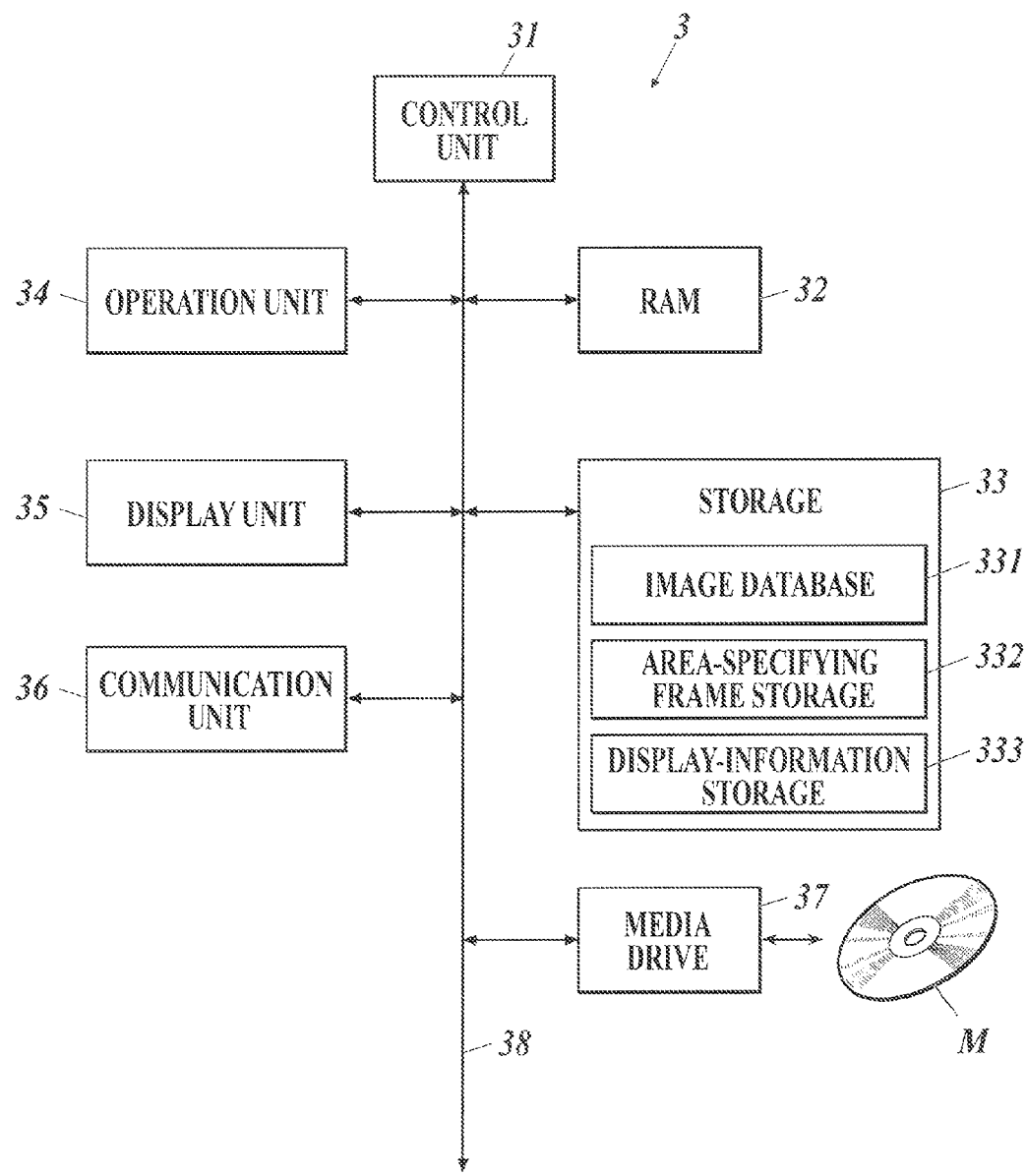
FIG. 2 is a block diagram showing a functional configuration of a radiographic-image processing device in FIG. 1.

FIG. 2 is a block diagram showing a functional configuration of a radiographic-image processing device 3.

As shown in FIG. 2, the radiographic-image processing device 3 includes a control unit 31, a RAM (Random Access Memory) 32, the storage 33, an operation unit 34, a display unit 35, a communication unit 36, a media drive 37 and so on. These parts and the like are connected via a bus 38.

The control unit 31 includes a CPU (Central Processing Unit) etc. which is not shown in drawings. The control unit 31 reads programs such as a system program, a processing program, etc. stored in the storage 33 and opens the programs in the RAM 32. Then the control unit 31 executes a variety of processing such as an initial-image generation processing, which will be explained later, following the opened programs.

The RAM 32 functions as a work area which temporarily stores a variety of programs, input or output data, parameters, etc. in the variety of processing that are executed and controlled by the control unit 31. The programs are read from the storage 33 and is able to be executed by the control unit 31.

The RAM 32 stores a patient information list received by the acceptance device 4.

The storage 33 includes a HDD (Hard Disk Drive), a nonvolatile memory of a semiconductor, and so on. The storage 33 stores a variety of programs as described above. In addition, the storage 33 stores parameters for image processing (such as a lookup table defining a gradation curve used for gradation processing), etc. which are used for adjusting definition of the radiographic image to be suited for diagnoses.

The storage 33 also stores irradiated-field-including-area information calculated in irradiated-field-including-area determination processing (details will be explained later), display-position information set in display-area setting processing (details will be explained later), etc.

The storage 33 includes an image database 331, an area-specification frame storage 332, a display-information storage 333, etc.

The image database 331 is a database which stores a variety of images, etc.

The variety of images includes the radiographic image (also referred to as an original image) sent from the modality 2, an initial image generated on the basis of the original image, a thumbnail image generated on the basis of the original image, etc.

The original image is stored in the image database 331. The original image is the radiographic image sent from the modality 2 on which no image processing has been executed.

The initial image is a diagnostic image which is used by a doctor for an X-ray interpretation and for obtaining informed consent from a patient. The initial image is obtained by executing predetermined image processing (such as an initial-image generation processing, which will be explained later) on the original image. When a doctor executes further image processing on the initial image, the doctor can overwrite data with the image on which the image processing is executed.

The image database 331 has an image information table 331a which stores a variety of information concerning images stored in the image database 331.

FIG. 3 shows an example of an image information table 331a.

The image information table 331a includes a "RECORD NO." field, an "UID" field, an "IMAGING DATE AND TIME" field, an "EXAMINATION ID" field, an "EXAMINATION PART" field, a "PATIENT ID" field, . . . an "ORIGINAL IMAGE" field, an "INITIAL IMAGE" field, a "THUMBNAIL IMAGE" field, etc. These field information are gathered in one record and are stored in the image information table 331a.

The "ORIGINAL IMAGE" field stores information which indicates a region where a file of the original image is stored.

The "INITIAL IMAGE" field stores information which indicates the region where a file of the initial image is stored. The "THUMBNAIL IMAGE" field stores information which indicates the region where a file of the thumbnail image is stored.

When the image database 331 stores an image, the image information table 331a stores information at the same time.

The information stored in the image information table 331a relates the original image, the initial image and the thumbnail image to an UID which is used for distinguishing patient information and images. Thereby the images can be searched by key information such as patient information, an imaging date, etc.

The area-specification frame storage 332 stores area-specification frames with which an area of a predetermined size is specified for the original image in irradiated-field recognition processing, which will be explained later. The area-specification frames are, for example, many kinds of rectangular frames (hereinafter referred to as rectangle R ($R_1, R_2, \ldots$)). The many kinds of rectangles R differ in size (area).

A form of the area-specification frame is not limited to a rectangle but can be a circle, an oval, etc., for example.

The display-information storage 333 stores many kinds of display information which are used in the display-area setting processing, which will be explained later, for determining a form and a size of the initial image which is to be displayed.

The display information includes information defining a form and a size of the image, such as a length, a width, an area and an aspect ratio of the image. This display information is set in advance so that the image suits a form and a size of a viewer window 351 (later explained) of the display unit 35. The image displayed in the viewer window 351 has a form and a size defined by specific display information among the many kinds of display information.

The many kinds of display information define forms and sizes of images which have been displayed in the viewer window 351, such as a rectangle, a size thereof, etc. corresponding to a cassette and a film that are used in CR (Computed Radiography) device. In this embodiment, the display-information storage 333 stores, for example, eight kinds of such display information. In the display-area setting processing which will be explained later, the display information storage 333 is used for reference, and then a display area of the initial image is set. The number of the display information is not limited to this. Further, the display information is free to be added, deleted and changed.

The operation unit 34 includes a keyboard which has cursor keys, numeral keys, a variety of function keys, etc., and a pointing device such as a mouse. The operation unit 34 outputs pushdown signals and operation signals to the control unit 31 as input signals. The pushdown signals are generated by pushing down keys of the keyboard. The operation signals are generated by operating the mouse. The control unit 31 changes the initial image G1 which is displayed in the viewer window 351 (later explained) of the display unit 35 in accordance with an operation by a user (such as a doctor) on the operation unit 34. Since the control unit 31 executes such processing, the control unit 31, together with the operation unit 34, functions as a display-change unit.

The display unit 35 has a monitor such as a CRT (Cathode Ray Tube) and a LCD (Liquid Crystal Display). The display unit 35 displays a variety of images on a screen in accordance with commands of display signals input from the control unit 31.

Figure 4:
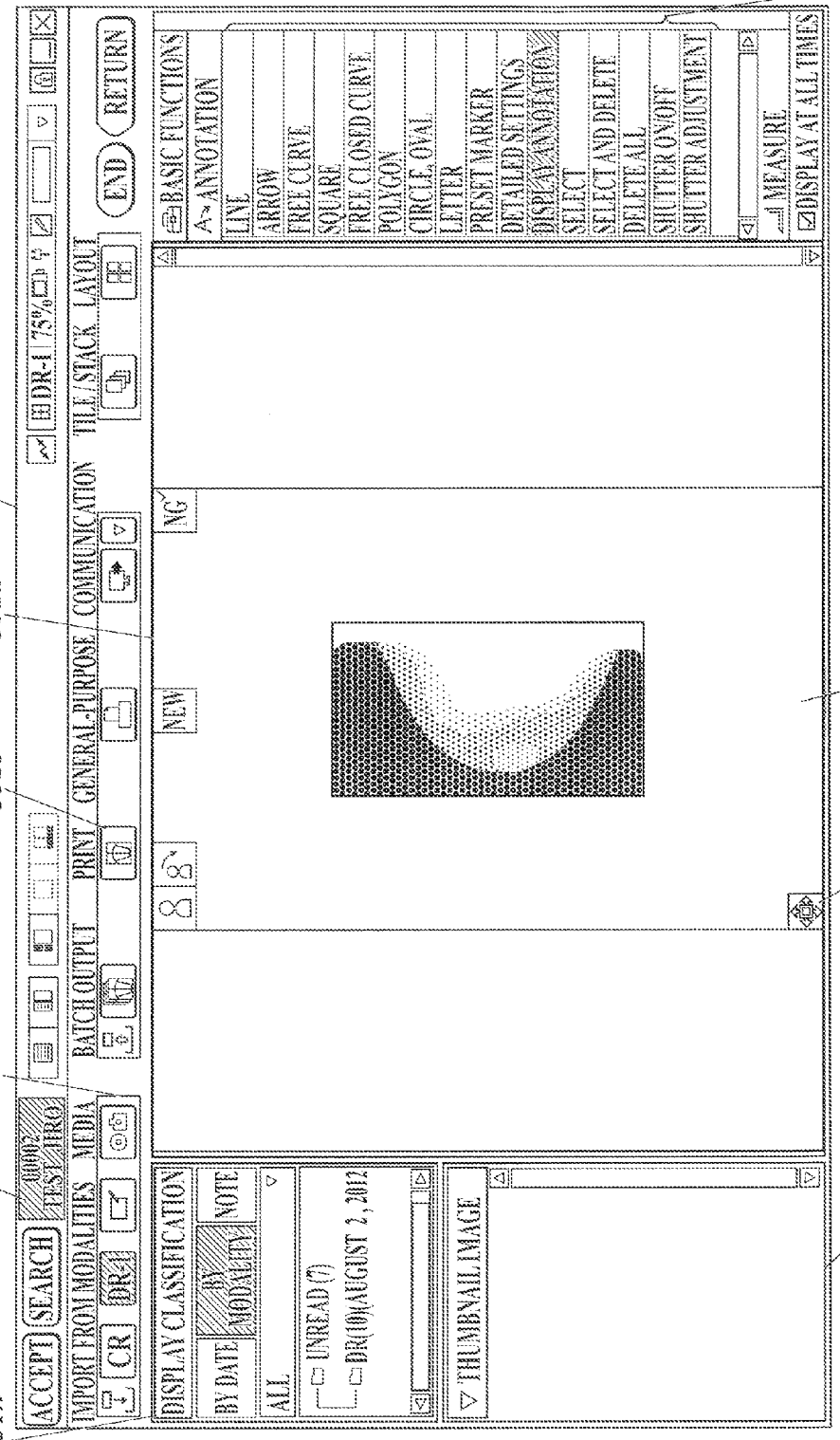
FIG. 4 shows an example wherein an initial image is displayed in a viewer window of a display unit in FIG. 2.

FIG. 4 shows an example of a viewer window 351 displayed on the display unit 35.

The viewer window 351 is displayed by selecting patient information which corresponds to a patient who is a diagnostic subject from a patient list window using the operation unit 34. The patient list window (a window wherein a patient information list which is sent from the acceptance device 4 is displayed) is displayed on the display unit 35 by a predetermined operation on the operation unit 34. The viewer window 351 is used for displaying the initial image, which is a diagnostic image, in several cases—for example, when a doctor carries out an X-ray interpretation, or when a doctor obtains informed consent from a patient.

The viewer window 351 is provided with, for example, an image display section 351a which displays an image, an image capture button 351b, a variety of tool buttons 351d, a print button 351e, a patient display section 351f, a thumbnail display section 351g, a display-image selection section 351h, etc.

The image display section 351a is a section which displays the original image captured from the modality 2, the initial image, a past image of the same patient, etc.

The image capture button 351b is a button for a command to capture the original image sent from the modality 2 as an image of a patient who is being a diagnostic subject (a patient who is displayed in the patient display section 351f). When the image capture button 351b is pushed down, the original image is captured as an image of a patient who is being the diagnostic subject, the original image being sent from the modality 2 until the image capture button 351b is pushed down again to give a command to stop capturing or until the viewer window 351 is closed or replaced by another window.

The variety of tool buttons 351d are buttons for executing image processing, such as contrast adjustment processing for shades of color or definition adjustment processing, on the displayed radiographic image. When a button of a designated item among the tool buttons 351d is pushed down, an input section, buttons, tool bars, etc. corresponding to the item is displayed. When input on the displayed input section or operation of buttons, tool bars, etc. is carried out through the operation unit 34, processing corresponding to the operation is executed on the displayed image. For example, when a shade-contrast button is pushed down, a slide bar for adjusting shades, a slide bar for adjusting contrast, etc. are displayed. When the slide bars are operated through the operation unit 34, the control unit 31 adjusts shades and contrast of an image displayed in the image display section 351a in accordance with the operation.

A doctor can operate tool buttons 351d to adjust definition to a designated level when the doctor makes a diagnosis through an X-ray interpretation of the initial image which is displayed on the image display section 351a of the viewer window 351.

The print button 351e is a button for giving a command to print a selected image through the general-purpose printer 6.

The patient display section 351f is a section which displays patient information of a patient being selected as the diagnostic subject.

The thumbnail display section 351g is a section which displays thumbnail images of the same patient (including images obtained in the past) for selection of a radiographic image which is to be displayed in the image display section 351a.

The display-image selection section 351h is a section for selecting a classification (for example, by date, by modality, etc.) of images to be displayed in the thumbnail display section 351g.

FIG. 4 shows an example wherein the initial image G1 is displayed in the image display section 351a.

The initial image G1 is an enlarged image obtained by enlarging a predetermined area including an irradiated field (an interest area) of the original image. The initial image G1 is the first diagnostic image to be generated and be displayed in initial-image generation processing after the original image is sent from the modality 2. The initial-image generation processing will be explained later.

The irradiated field is an area where an X-ray reaches through a subject. Diagnosis can be made more conveniently by using the initial image G1, which is obtained by enlarging a predetermined area including the irradiated field, as the diagnostic image.

An indicator A1 which indicates that the initial image G1 is not the original image is displayed in the initial image G1. The indicator A1 functions as a recognition section which makes a user recognize that the initial image G1 is an enlarged image.

A user (a doctor, etc.) can replace the displayed initial image G1 by switching the indicator A1 on and off using the operation unit 34.

Figure 5:
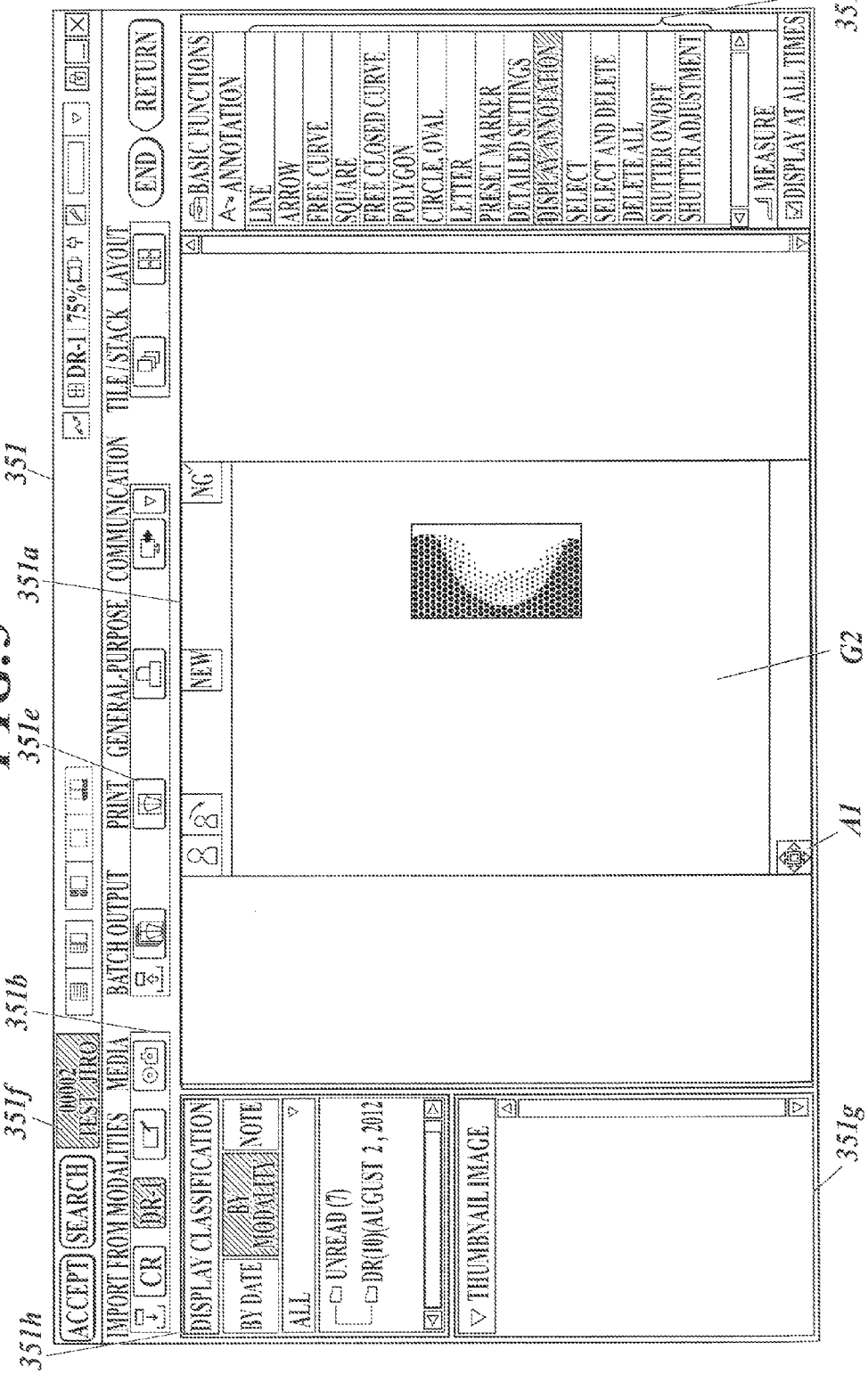
FIG. 5 shows an example wherein the initial image in FIG. 4 is switched to the whole image.

Specifically, when the indicator A1 is pushed down (ON operation), the initial image G1 is replaced by the original image G2 as shown in FIG. 5.

In the original image G2 displayed as a result of the operation, an indicator A1 being pushed down is displayed. A user can make the original image G1 be displayed again by an operation of releasing push-down of the indicator A1 in the original image G2 (OFF operation).

Figure 6:
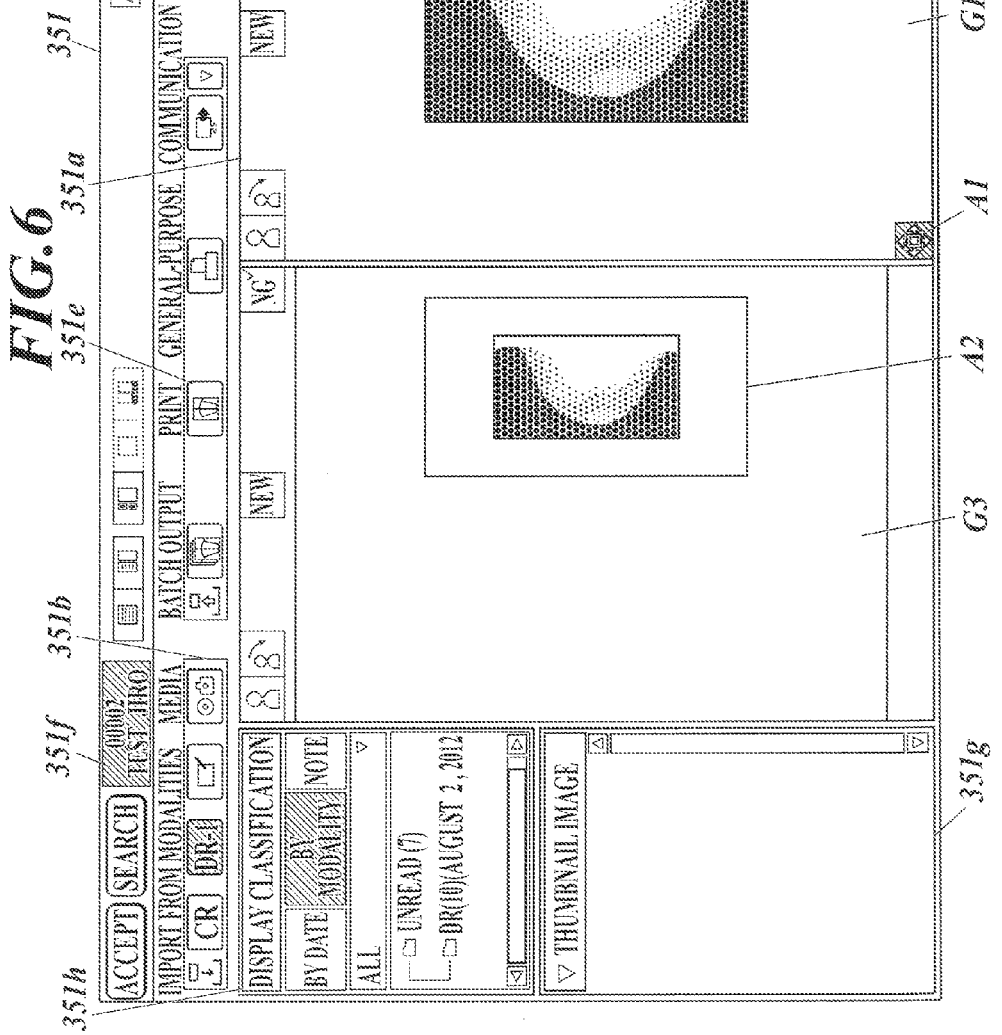
FIG. 6 shows an example wherein a reference image is displayed together with the initial image in FIG. 4.

It may be configured that a displayed image is switched such that, when the indicator A1 is pushed down (ON operation), a reference image G3 is displayed with the original image G1 as shown in FIG. 6. In the reference image G3, a frame A2 is displayed. The frame A2 shows which area in the original image the initial image corresponds to. The initial image is obtained by enlarging a certain area in the original image.

While the reference image is displayed, an indicator A1 being pushed down is displayed in the initial image G1. A user can operate to return to the state wherein only the initial image G1 is displayed by an operation of releasing push-down of the indicator A1 in the initial image G1 (OFF operation).

As an example of image changing by the indicator A1, in addition to the above examples of FIG. 5 and FIG. 6, it may be configured that, when the indicator A1 is pushed down (ON operation), switching is executed such that the original image G2 is displayed together with the initial image G1.

The initial image G1 moves in the image display section 351a in accordance with a predetermined operation by a user using the operation unit 34. A display magnification of the initial image G1 changes in accordance with a predetermined operation by a user using the operation unit 34.

The communication unit 36 includes a network interface, etc. and sends and receives data from outer equipment which is connected to the network 8 via a switching hub.

A portable storage medium M, such as a CD-R (Compact Disk Recordable), a DVD-R (Digital Versatile Disk Recordable) or a MO (Magnet Optical) disk, can be inserted and be taken out of the media drive 37. The media drive 37 reads or writes data from or on the storage medium M being inserted.

The acceptance device 4 is a computer device which executes entry registration of a patient who visits a hospital, accounts, calculation of insurance points, etc. The acceptance device 4 includes a storage unit which consists of a CPU, a ROM, a RAM, etc., an input unit which consists of a keyboard, a mouse, etc., a display unit which consists of a CRT, a LCD, etc., a communication unit which controls communications with devices connected to the network 8 (not shown in the drawings), etc. When displaying of an acceptance input window is commanded from the input unit, the acceptance device 4 displays the acceptance input window (not shown in the drawings) on the display unit in cooperation with the CPU and programs stored in the storage unit. When acceptance information (such as an acceptance number and a patient name) is input from the input unit through the acceptance input window, the acceptance device 4 generates (updates) a patient information list of accepted patients and stores the list in the storage unit. Then the communication unit sends the list to the image display device 3 as the occasion demands.

The imager 5 is a fuel-and-lighting film printer. The imager 5 records a latent image by exposing a transmission recording medium (film) using a laser on the basis of the radiographic image sent from the image display device 3. Then the imager 5 visualizes the latent image by heat phenomenon processing.

The general-purpose printer 6 records an image on a reflex recording medium (such as a paper medium or a seal) by ink-jet printing or laser printing.

The client PC 7 is, for example, a computer device which displays the radiographic image sent from the radiographic-image processing device 3.

<Examination Flow Using In-Facility System 1>

Next, an examination flow (1) to (5) in a medical facility with the in-facility system 1 installed therein will be explained.

(1) First, a patient is accepted at a reception. Patient information of the accepted patient is input through the acceptance device 4. A patient information list including this patient information is sent to the radiographic-image processing device 3. After being sent from the acceptance device 4, the patient information list is stored in the RAM 32 of the radiographic-image processing device 3.

(2) Next, diagnosis and necessary examinations are determined in a diagnostic room. The diagnosis includes an interview, reviewing a patient's past chart, an image, a report, etc.

(3) Next, the modality 2 executes X-ray imaging of an affected part (imaging subject part) of a patient in the diagnostic room. As described later, the radiographic-image processing device 3 can generate an initial image suitable for X-ray interpretation, no matter how large or small the imaging subject part of a subject patient is. Therefore, when imaging is executed, the modality 2 can image in a fixed imaging condition and does not need adjustment between each imaging.

(4) After the X-ray imaging, the original image which has been obtained in the imaging is captured in the radiographic-image processing device 3, goes through initial-image generation processing which will be explained later, and is output.

(5) Diagnosis or medical treatment is carried out on the basis of the output initial image.

<Operation of Radiographic-Image Processing Device 3>

Next, an operation of the radiographic-image processing device 3 will be explained.

The radiographic-image processing device 3 according to the embodiment executes initial-image generation processing.

The modality 2 images in a fixed imaging condition and adjustment is not carried out between each imaging. Therefore qualities of original images differ one by one in accordance with different affected parts (imaging subject parts) of a patient and with different amounts of emitted X-rays caused by change in device characteristics of the modality 2, etc. If qualities of images used for X-ray interpretation differs one by one, the X-ray interpretation cannot be carried out stably. Therefore, in order to stably output images suitable for X-ray interpretation, the radiographic-image processing device 3 executes initial-image generation processing executing image processing on the original image to generate an initial image which satisfies a predetermined standard as a diagnostic image. A doctor can confirm whether imaging is successful or not (additional imaging is needed or not) by displaying the initial image in the image display section 351a of the viewer window 351 to observe the initial image.

Hereinafter, the initial-image generation processing will be explained in detail.

Before this initial-image generation processing, the viewer window 351 for a patient who is the diagnostic subject is displayed on the display unit 35, and the image capture button 351b in the viewer window 351 is pushed down using the operation unit 34. Also, the original image, obtained by imaging of the modality 2, is captured, made to be related to patient information of a patient selected in the patient list window and stored in the image database 331.

Figure 7:
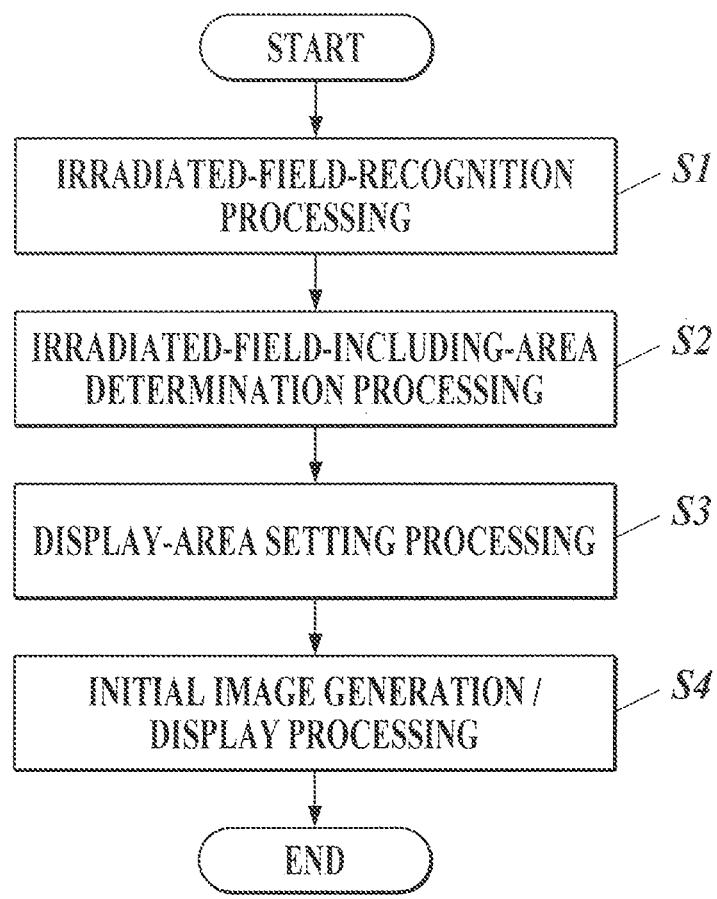
FIG. 7 shows a flowchart of initial-image generation processing.

FIG. 7 shows a flowchart of the initial-image generation processing. FIG. 8A to FIG. 8D are schematic views of the initial-image generation processing.

The initial-image generation processing is executed by the control unit 31 in cooperation with programs stored in the storage 33. The control unit 31 functions as an enlargement display unit since the control unit 31 executes the initial-image generation processing.

First, at Step S1, the control unit 31 executes irradiated-field recognition processing on the original image (FIG. 8A) to recognize the irradiated field on the original image (FIG. 8B).

Next, at Step S2, the control unit 31 executes irradiated-field-including-area determination processing on the irradiated field recognized at the above Step S1 to determine an area (irradiated-field-including area) which has the minimum size that can include the irradiated field and which is in an upright position in relation with the viewer window 351 (FIG. 8C).

Next, at Step S3, the control unit 31 executes display-area setting processing to set a display area of the initial image which is to be displayed in the image display section 351a on the basis of the size of the irradiated-field-including-area determined at the above Step S2.

Next, at Step S4, the control unit 31 executes initial-image generation and display processing to generate the initial image (FIG. 8D) and to display the initial image in the image display section 351a.

Hereinafter, respective processing at the above Steps S1 to S4 will be explained in detail.

<Irradiated-Field Recognition Processing>

Figure 9:
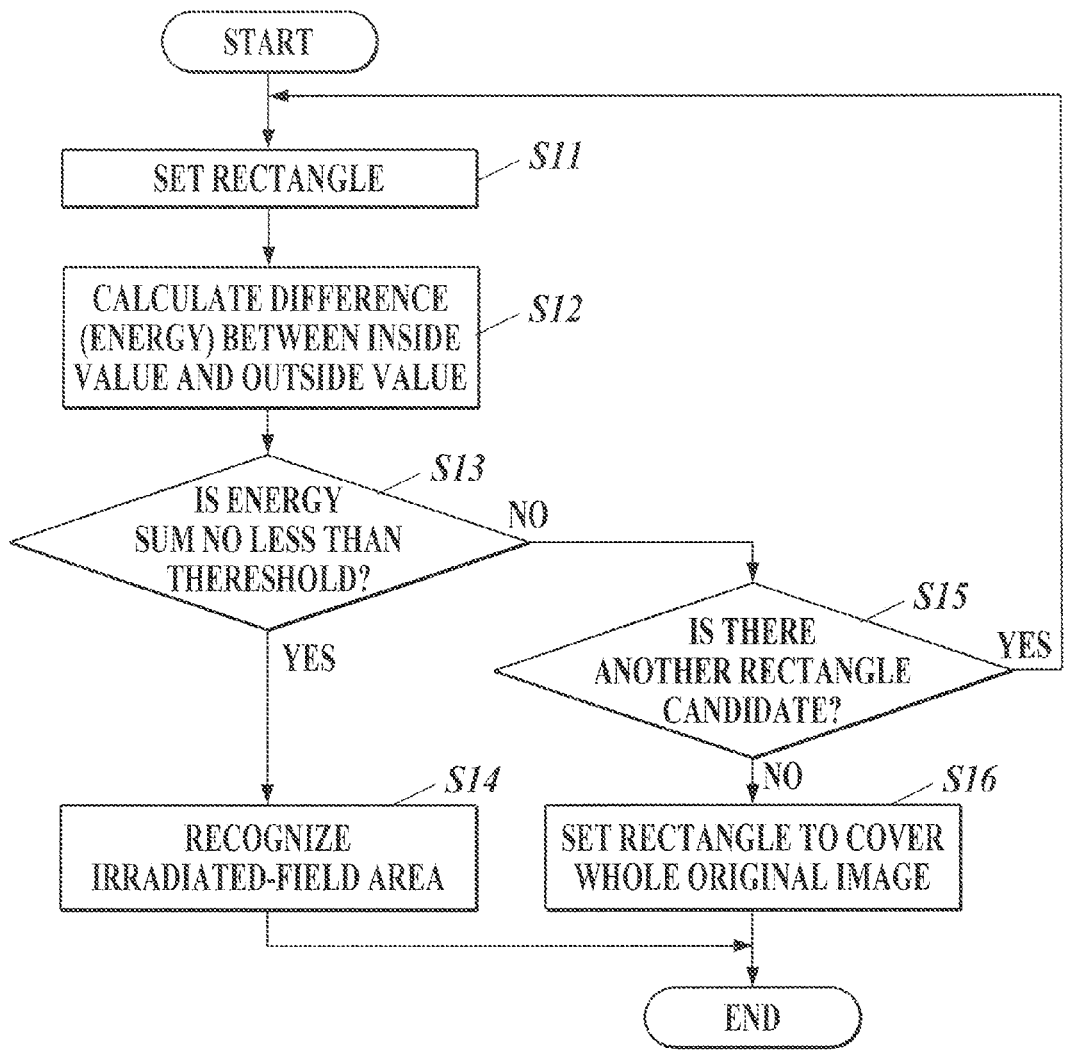
FIG. 9 shows a flowchart of irradiated-field recognition processing.

FIG. 9 shows a flowchart of irradiated-field recognition processing.

The initial-image generation processing is executed by the control unit 31 in cooperation with programs stored in the storage 33.

In the irradiated-field recognition processing, the irradiated field in the original image is distinguished.

This is because, when a variety of affected parts (imaging subject parts) of a patient are imaged using a FPD of a single fixed size, a position of the irradiated field on the original image does not always come to the center of the original image. Also, the irradiated fields vary in size.

First, at Step S11, the control unit 31 sets a rectangle R having a predetermined size on the original image.

Specifically, the control unit 31 selects a rectangle R which is not yet used in the irradiated-field recognition processing on the image and which has the minimum size (area) among many kinds of rectangles R (R1, R2, . . . ) stored in the area-specification frame storage 332 of the storage 33. Then the control unit 31 sets the rectangle R at the start position on the original image (see the portion shown by solid lines in FIG. 10).

The start position is where the rectangle R is set in the beginning for executing the irradiated-field recognition processing, and can be anywhere on the original image, for example, the position at which the left upper corner of the rectangle coincides with the left upper corner of the original image.

Next, at Step S12, the control unit 31 moves the rectangle R which is set at the above Step S1 on the original image (see the portion shown by dotted lines in FIG. 10). In this while, at several points on the original image, the control unit 31 calculates energy which is defined as an amount of difference between an inside value and an outside value. The inside value is calculated using radiographic data inside the rectangle R. The outside value is calculated using radiographic data outside the rectangle R.

Hereinafter, "Ri" indicates the "i"$^{th}$ rectangle among the many kinds of rectangles R. Also, a position of the rectangle on the original image is expressed as "r=(x, y)". The above difference amount (energy E (Ri, r)) is expressed by the following formula (1).

[FORMULA 1]

$$E(R_i,r)=I(R_i,r)-O(R_i,r) \quad (1)$$

I($R_i$,r): INSIDE VALUE
O($R_i$,r): OUTSIDE VALUE

The inside value (I (Ri, r)) is a statistic which reflects an average radiation dose in the radiographic data inside the rectangle R, that is, specifically, an average value of brightness signals corresponding to a radiation dose inside the rectangle R.

The processing can be made faster by defining the inside value as an average value of brightness signals corresponding to a radiation dose inside the rectangle R. Because known moving-average filter (also called as leveling filter or smoothing filter) processing etc. can be applied.

Hereinafter, moving-average filter processing will be explained. The moving-average filter processing is a method wherein an average value of brightness values around an interest pixel is calculated and used as a brightness value of an image on which the processing has been executed.

For example, in a case of a moving-average filter having a kernel of five-by-five pixels as shown in FIG. 11A, brightness values of five-by-five pixels around an interest pixel are added up. Then the sum is divided by the number of pixels (5×5=25). This processing is executed on all pixels by raster-scanning.

As shown in FIG. 11B, when a subject of the processing moves to an adjoining interest pixel, some of the pixels added in the calculation are duplicates of the pixels which were added in the calculation for the former interest pixel. Therefore, the sum of brightness values in the processing for the former interest pixel is stored. The sum of brightness values of a pixel line on the left edge of the kernel is subtracted from the sum of the brightness values calculated for the former interest pixel. Then the sum of brightness values of a pixel line on the right edge of the subject kernel is added. Thereby the sum of brightness values of the pixels in the present kernel is obtained.

In the former example, addition is done twenty five times for calculating the sum of brightness values of pixels in a kernel. On the other hand, in the latter example, the processing can be finished by performing subtraction five times and performing addition five times, that is, ten times in total. The larger the size of the kernel is, the more remarkable the effect is.

Further, the processing can be made even faster by storing the sum of brightness values of a horizontal line in an image since similar processing can be executed when the processing moves in the vertical direction.

It goes without saying that the average value can be calculated without applying the above moving-average filter processing.

The outside value (O (Ri, r)) is a statistic which reflects a radiation dose in an area wherein a radiation dose in radiographic image data outside the rectangle R is larger than any other areas, that is, specifically, the maximum value of a brightness signal which corresponds to a radiation dose outside the rectangle R.

The processing can be made faster by defining the outside value as the maximum value of a brightness signal which corresponds to a radiation dose outside the rectangle R. Because the following method can be applied.

Figure 12A:
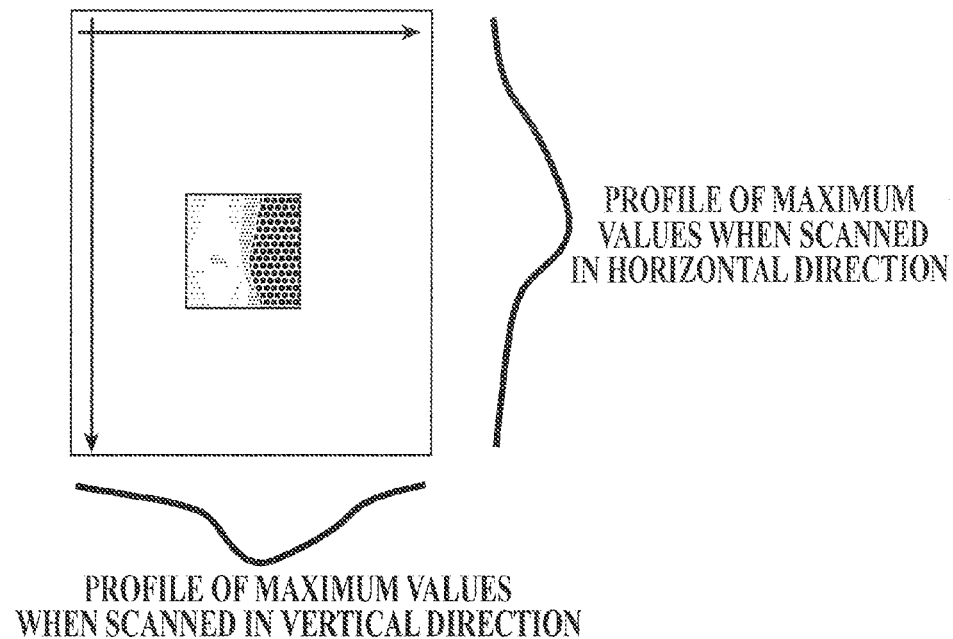
FIG. 12A and FIG. 12B illustrate a preferable calculation method of an outside value.

First, as shown in FIG. 12A, the original image is scanned in a vertical direction. The maximum value among brightness values of scanned portions is extracted. This processing is executed for every predetermined line (such as a single line of pixels) to generate a profile of maximum values. Also, the original image is scanned in a horizontal direction. The maximum value among brightness values of scanned portions is extracted. This processing is executed for every predetermined line (such as a single line of pixels) to generate a profile of maximum values.

Figure 12B:
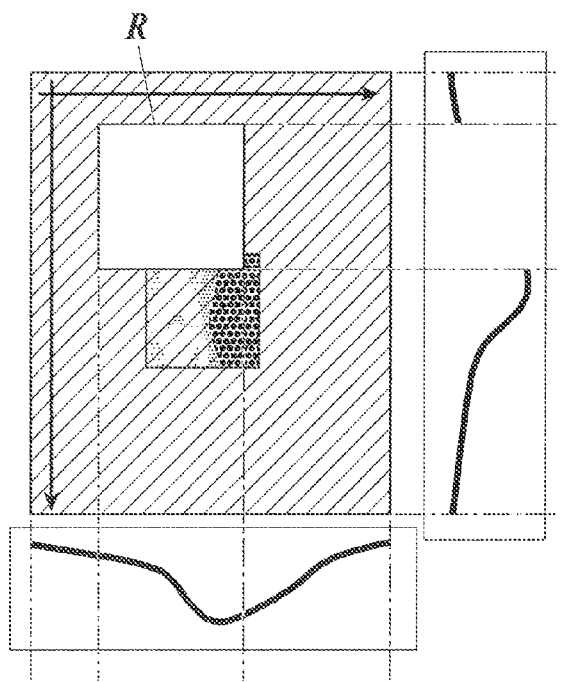

Then, as shown in FIG. 12B, a portion where the rectangle R exists is deleted from the profile, and the maximum value among the remaining profile is extracted. That is the maximum brightness value outside the rectangle R.

The larger the ratio of the irradiated-field to the rectangle R is, the larger the inside value is. The outside value is at the minimum when there is no irradiated-field area outside the rectangle R.

Figure 13A:
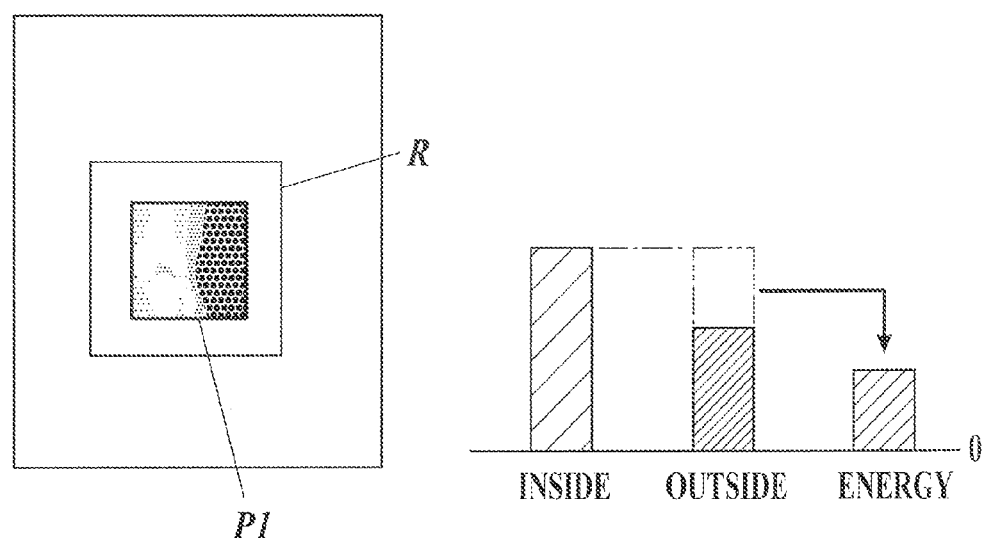
FIG. 13A and FIG. 13B illustrate the inside value, the outside value and energy.
Figure 13B:
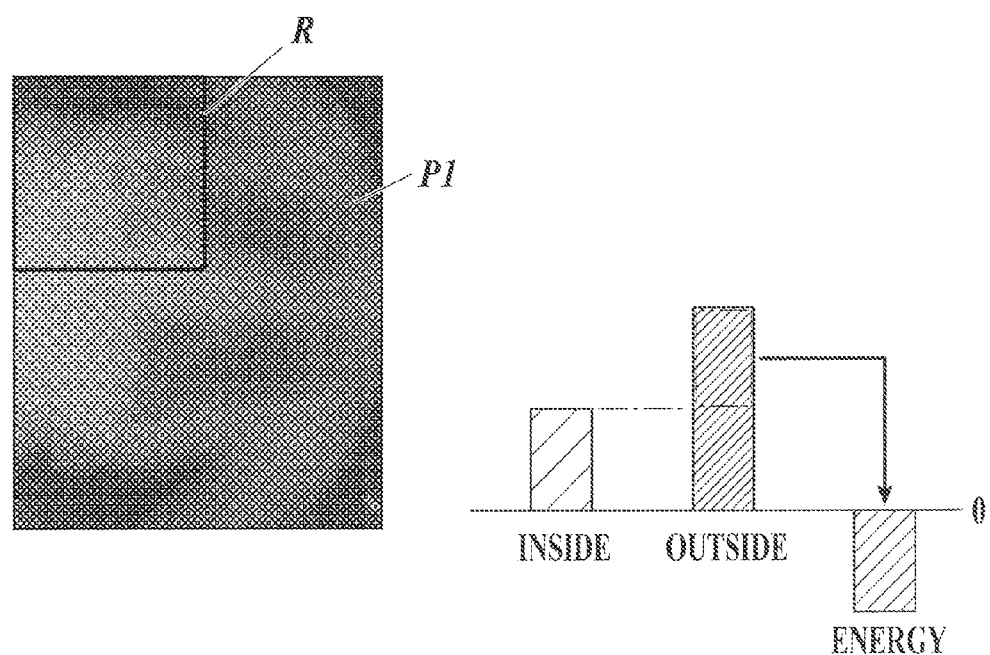

Accordingly, as shown in FIG. 13A, when the difference between the inside value and the outside value is no less than 0, it is highly probable that the rectangle R is surrounding the irradiated field. Also, as shown in FIG. 13B, when the difference between the inside value and the outside value is less than 0, it is highly probable that the rectangle R is not surrounding the irradiated field.

After the rectangle R is set at the start position on the original image at the above Step S1, the control unit 31 calculates the above energy E (Ri, r) at the start position. Then the control unit 31 moves the rectangle R for a predetermined distance, and calculates the energy E (Ri, r) at the arrival position in the same manner. The control unit 31 repeats the operation. Thus the control unit 31 calculates the energy E (Ri, r) at many points on the original image while moving the rectangle R all over the original image.

Figure 14:
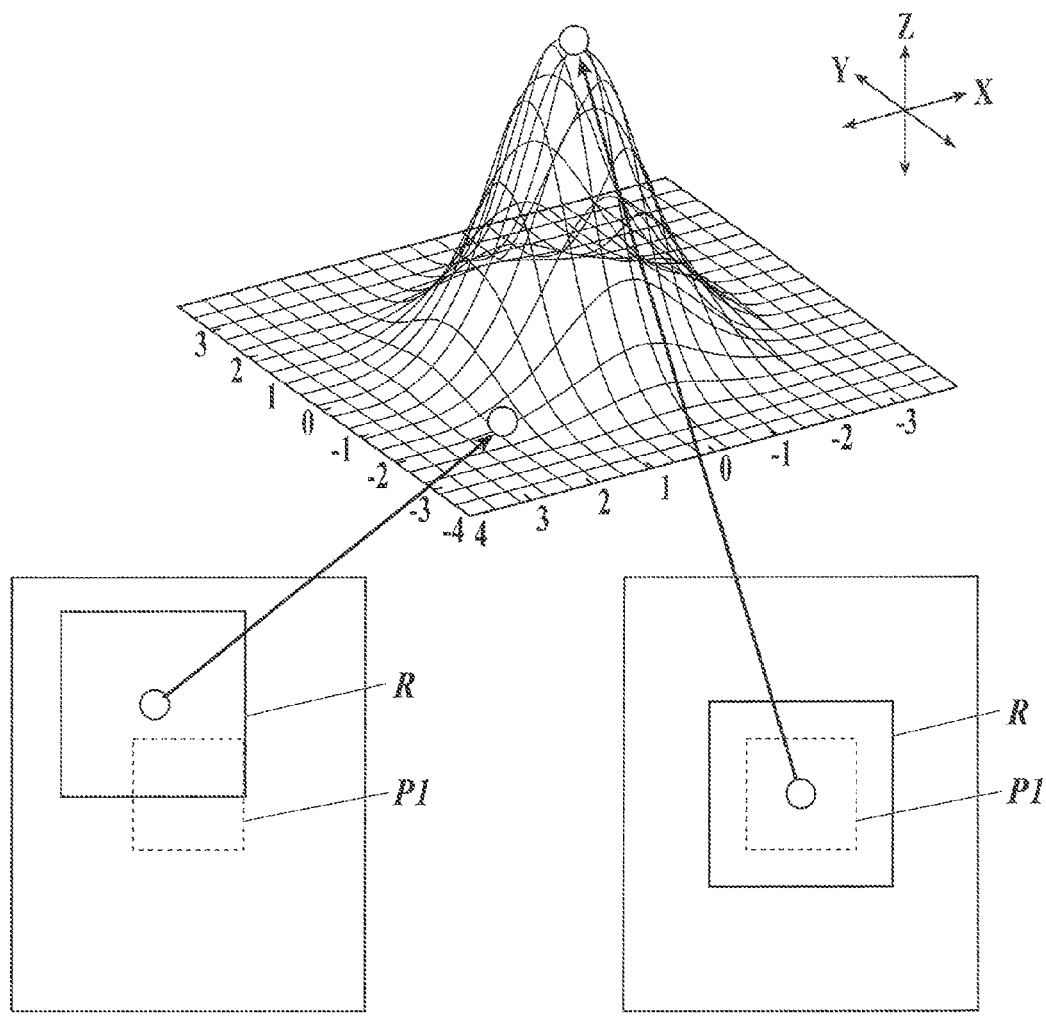
FIG. 14 shows an example plot of energy.

FIG. 14 shows an example plot of energy E (Ri, r) calculated for several points on the original image.

FIG. 14 is an example showing a three-dimensional profile obtained when the rectangle R includes the irradiated-field P1 at the center portion of the original image. Since the energy E (Ri, r) is the difference between the inside value and the outside value, if there is a position at which the rectangle R includes the irradiated-field P1, a profile having the high peak of energy E (Ri, r) can be obtained as shown in FIG. 14.

Next, at Step S13, the control unit 31 calculates the sum of energy E (Ri, r) that are calculated for several points on the original image, and determines whether the sum of energy E (Ri, r) is no less than a predetermined threshold or not.

The threshold is set in advance on the basis of radiation intensity etc. at the time the image is captured.

The minimum value of energy is set at 0 for calculating the sum of energy E (Ri, r).

When determining that the sum of energy exceeds the predetermined threshold (Step S13: YES), the control unit 31 sets a size and a position of the rectangle R and recognizes the irradiated area at Step S14, and then ends the processing.

As a method for setting a size and a position of the rectangle R, for example, a method of setting on the basis of weighted averaging of energy or a method of setting on the basis of maximum energy value can be adopted.

First, the method of setting on the basis of weighted averaging of energy will be explained.

FIG. 15A shows an example of a graph wherein a position of the rectangle R on the original image is the horizontal axis, and wherein energy calculated for each position is the vertical axis. According to the graph, an area of the sum of all the peaks (the hatched part in FIG. 15A) shows the sum of energy E (Ri, r).

As shown in FIG. 15A, when the sum of energy E (Ri, r) exceeds the threshold, the control unit 31 sets a size of a rectangle R by averaging sizes of rectangles R which have been used for processing. This averaging is accompanied by weighting such that a rectangle R of a certain size which has larger energy E (Ri, r) is weighted more following the formula (2) below. Also, the control unit 31 sets a position of a rectangle R by averaging positions of rectangles R which have been used for processing. This averaging is accompanied by weighting such that a position wherein larger energy E (Ri, r) is detected is weighted more following the formula (3) below.

[Formula 2]

$$\hat{R} = \frac{\sum_i \sum_r R_i \times E(R_i, r)}{\sum_i \sum_r E(R_i, r)} \quad (2)$$

[Formula 3]

$$\hat{r} = \frac{\sum_i \sum_r r \times E(R_i, r)}{\sum_i \sum_r E(R_i, r)} \quad (3)$$

The following is an example of an advantage of such method.

In this processing, energy values of rectangles R are calculated for the original image one by one from a small rectangle R to a large rectangle R. Therefore, when the energy sum of one rectangle R is nearly same as the threshold but is less than the threshold, a calculation using a rectangle R of the next size is executed. A size of a rectangle R which has the energy sum less than the threshold and is closest to the threshold can be set by the above weight averaging. Also, a position of a rectangle R can be set such that the center of the rectangle R comes to the center of the irradiated area.

Thus a size and a position of a rectangle R is set, and the control unit 31 determines an area which is on the original image and is included in the rectangle as the irradiated-field-including area.

Next, a method of setting on the basis of maximum energy value will be explained.

FIG. 15B shows an example of a graph wherein a position of the rectangle R on the original image is the horizontal axis, and wherein energy calculated for each position is the vertical axis. According to the graph, an area of the sum of all the peaks (the hatched part in FIG. 15B) shows the sum of energy E (Ri, r).

As shown in FIG. 15B, when the sum of energy E (Ri, r) exceeds the threshold, the control unit 31 sets a size of a rectangle R to the size of a rectangle R which shows the maximum energy E (Ri, r) (that is to say, a rectangle R which shows the maximum energy E (Ri, r) among rectangles having been used in the processing) following the formula (4) below. A position of the rectangle R is set according to a position where energy E (Ri, r) of the rectangle R is at the maximum.

[FORMULA 4]

$$(\hat{R}, \hat{r}) = \arg_{i,r} \max E(R_i, r) \quad (4)$$

An advantage of the method is that the processing can be faster since a calculation processing for setting a size and a position of a rectangle R is simple.

Thus a size and a position of a rectangle is set, and the control unit 31 determines an area which is on the original image and is included in the rectangle as the irradiated-field-including area.

When determining that the energy sum is less than a predetermined threshold (step S13: NO) at the above. Step S13, the control unit 31 determines whether or not there is a rectangle R (another rectangle candidate) which is not yet used for the radiation-field recognition processing in the area-specification frame storage 332 of the storage 33 at following Step S15. When the control unit 31 determines that there is another rectangle candidate (step S15: YES), the processing returns to the above Step S11 and the steps thereafter are repeated.

On the other hand, when the control unit 31 determines that there is no other rectangle candidate (step S15: NO), the control unit 31 sets a rectangle R such that the rectangle R covers the whole screen (that is to say, the whole screen is set as the irradiated-field area) at Step S16, and ends the processing.

FIG. 16 shows an image example which has no area other than the irradiated field.

As shown in FIG. 16, as for the image which has no area other than the irradiated field, the energy sum does not exceed the threshold. Accordingly, the energy sum does not exceed the threshold at the above Step S13, and calculation of energy using all kinds of rectangles R stored in the area-specification frame storage 332 is finished. At this time, the control unit 31 sets the whole image as an irradiated-field area. Thus, when an image has no area other than the irradiated field, the control unit 31 recognizes the whole area of the image as an irradiated-field, and does not separately set an irradiated-field area inside the original image.

In addition to the above irradiated-field recognition processing shown in FIG. 9, any known processing can be adopted as an irradiated-field recognition method. For example, as disclosed in the Japanese Patent Publication No. H5-7579, the processing may be consist of dividing the original image into small areas, calculating dispersion values for respective divided areas, and distinguishing the irradiated-field area on the basis of the calculated dispersion values. In general, amounts of X-ray which reaches areas other than the irradiated field are virtually uniform. Therefore dispersion values of the small areas are small. On the other hand, dispersion values of the small areas which include an edge of the irradiated-field area is large because a large amount of X-ray reaches at some portions (non-irradiated-field area) while a smaller amount of X-ray reaches at other portions (irradiated-field area). Therefore small areas having the dispersion value no less than a predetermined value is deemed to include an edge, and an area surrounded by these small areas is distinguished as an irradiated area.

A known irradiated-field recognition processing can be applied to the above irradiated-field recognition processing shown in FIG. 9. This is effective when the above irradiated-field recognition processing shown in FIG. 9 is executed on a relatively small number of points on the original image. In view of a processing speed, when the above irradiated-field recognition processing shown in FIG. 9 is executed on a relatively small number of points on the original image, an irradiated field larger than the actual irradiated field is distinguished. The irradiated field gets closer to an actual irradiated-field by additionally executing a known irradiated-field recognition processing on an irradiated field larger than the actual irradiated field.

As described above, an irradiated-field area in the original image can be distinguished by the irradiated-field recognition processing.

<Irradiated-Field-Including-Area Determination Processing>

Figure 17:
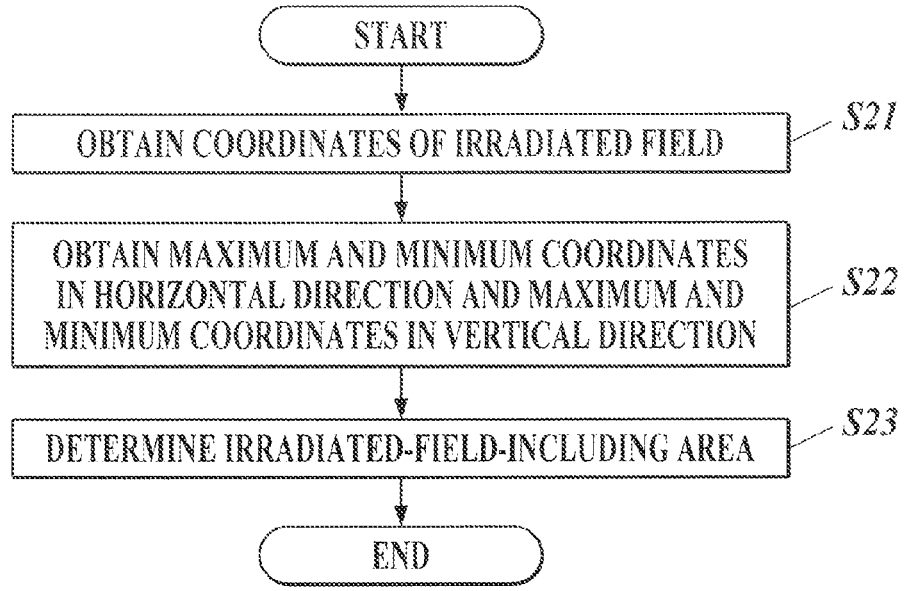
FIG. 17 shows a flowchart of irradiated-field-including-area determination processing.

FIG. 17 shows a flowchart of irradiated-field-including-area determination processing.

The irradiated-field-including-area determination processing is executed by the control unit 31 in cooperation with programs stored in the storage 33.

The irradiated-field-including-area determination processing is executed on an irradiated field recognized in the above irradiated-field recognition processing.

This is executed in view of a case that the irradiated field is not in an upright position in relation to an image, that is, a length direction and a width direction of the irradiated field are inclined with respect to the viewer window 351. An appropriate display area can be set in the following display-area setting processing by determining an area (irradiated-field-including area) which has the minimum size that can include the irradiated-field and which is in an upright position in relation to the viewer window 351.

First, at Step S21, the control unit 31 obtains coordinates of the irradiated area recognized in the above irradiated-field recognition processing.

Next, at Step S22, the control unit 31 obtains the maximum coordinate and the minimum coordinate in the horizontal direction and the maximum coordinate and the minimum coordinate in the vertical direction among the coordinates of the irradiated area, which are obtained at the above Step S21.

Next, at Step S23, the control unit 31 calculates the maximum width in the vertical direction and the maximum width in the horizontal direction of the irradiated field on the basis of the coordinates obtained at the above Step S22. The control unit 31 calculates an area and an aspect ratio using the calculated maximum width in the vertical direction and the calculated maximum width in the horizontal direction. The control unit 31 determines an area (irradiated-field-including area) which has enough size to include the irradiated-field and which is in an upright position, and ends the processing. The values calculated in this processing are stored in the storage 33 as irradiated-field-including-area information.

<Display-Area Setting Processing>

Figure 18:
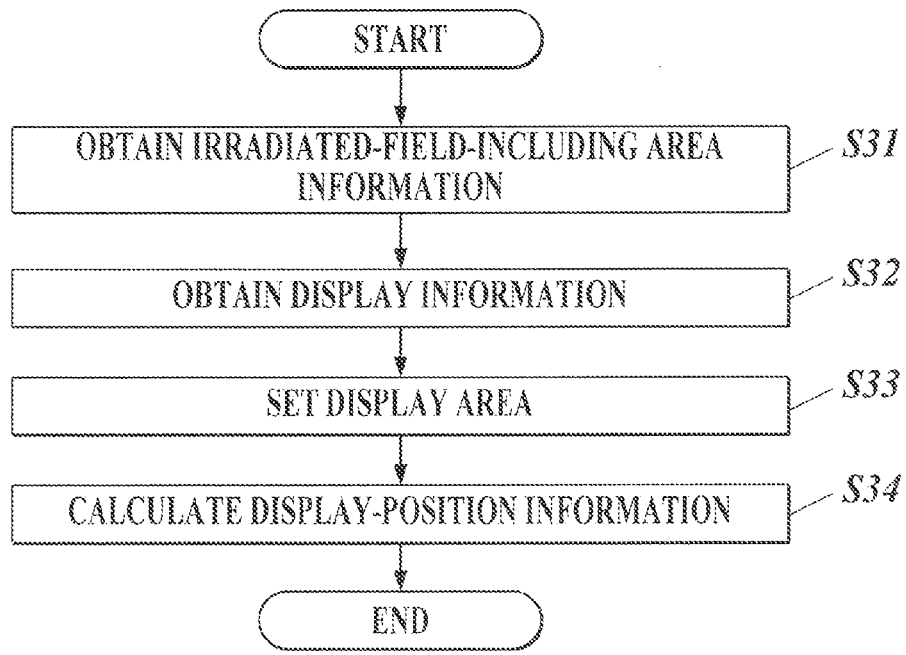
FIG. 18 shows a flowchart of display-area setting processing.

FIG. 18 shows a flowchart of display-area setting processing.

The display-area setting processing is executed by the control unit 31 in corporation with programs stored in the storage 33.

The display-area setting processing is executed on the irradiated-field-including area determined in the above irradiated-field-including-area determination processing.

This is executed in view of the fact that an image of a predetermined form and a predetermined size is appropriately displayed in the image display section 351a of the viewer window 351. As described above, many kinds of display information is stored in the display information storage 333, and an appropriate information is selected from the many kinds of display information in the display-area setting processing.

First, at Step S31, the control unit 31 refers to the storage 33 and obtains irradiated-field-including-area information calculated in the above irradiated-field-including-area determination processing.

Next, at Step S32, the control unit 31 obtains display information stored in the display information storage 333 of the storage 33 in advance. At this time, eight kinds of display information are obtained.

Next, at Step S33, the control unit 31 selects the most appropriate information among the display information obtained at the above Step S32, and sets a display area.

Specifically, among the eight kinds of display information, the control unit 31 selects information which includes a length, a width and an area value of an image no less than a length, a width and an area value of an irradiated-field-including area and which also includes the smallest area value and an aspect ratio nearest to an aspect ratio of the irradiated-field-including area. Then a display area of the original image is set on the basis of a form and a size of an image defined in this selected display information.

Next, at Step S34, the control unit 31 calculates coordinates on the original image in vertical and horizontal directions at the display start point, the display end point and the display center. Then the control unit 31 ends the processing.

That is to say, coordinates of the display start point and the display end point in vertical and horizontal directions in the original image, which are calculated in this processing, specifies a scope of the initial image in the original image. An area surrounded by coordinates of the display start point and the display end point in vertical and horizontal directions is a display area actually displayed in the image display section 351a of the viewer window 351 (a predetermined area including an irradiated field of the original image).

Coordinates in the original image in vertical and horizontal directions at the display start point, the display end point and the display center, which are calculated in this processing, are stored in the storage 33 as display-position information.

<Initial-Image Generation and Display Processing>

Figure 19:
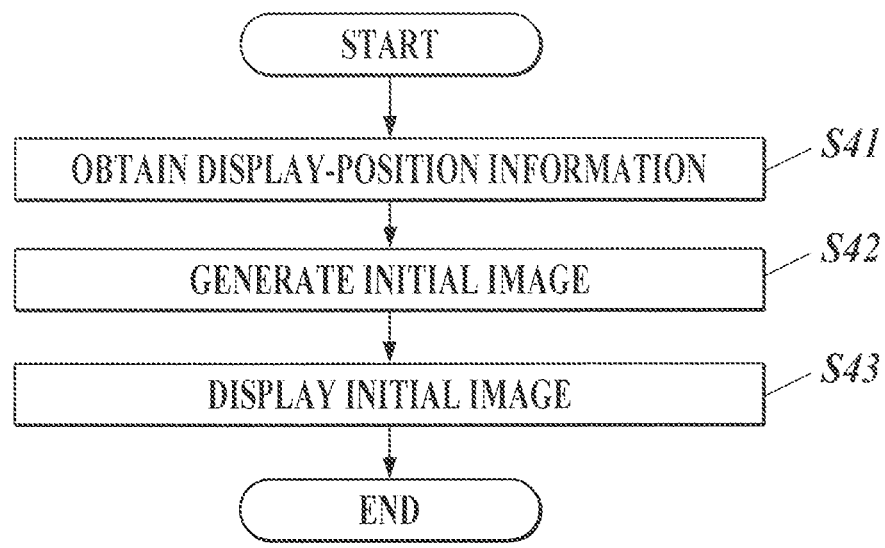
FIG. 19 shows a flowchart of initial-image generation and display processing.

FIG. 19 shows a flowchart of initial-image generation and display processing.

The initial-image generation and display processing is executed by the control unit 31 in corporation with programs stored in the storage 33.

This is processing of generating an initial image on the basis of the original image and displaying the initial image in the image display section 351*a* of the viewer window 351.

First, at Step S41, the control unit 31 refers to the storage 33 and obtains display-position information calculated in the above display-area setting processing.

Next, at Step S42, the control unit 31 generates an initial image.

Specifically, the control unit 31 generates an enlarged image obtained by enlarging an area surrounded by coordinates of the display start point and the display end point in vertical and horizontal directions in the original image (a display area actually displayed) to suit the image display section 351*a* of the viewer window 351.

The above "display area actually displayed" is an area shown by a frame A2 in the reference image G3 shown in FIG. 6.

Next, at Step S43, the control unit 31 displays the initial image, which is generated at the above Step S42, in the image display section 351*a* of the viewer window 351 (see FIG. 4), and ends the processing.

The initial image thus displayed is the first diagnostic image displayed in the image display section 351*a* of the viewer window 351 after the original image is imported to the radiographic-image processing device 3. The initial image is the first image that a user observes. As described above, the initial image is an image obtained by enlarging a predetermined area of the original image which includes an irradiated-field area, that is, an image obtained by extracting an area in the original image necessary for diagnosis. Therefore, problems—for example, a necessary portion of an image is too small to make a diagnosis—are prevented from occurring.

The indicator A1 as a recognition section is displayed in the initial image. Therefore a user can recognize at first glance that the initial image is an enlarged image obtained by enlarging a portion of the original image.

A user can change the initial image at will by carrying out a predetermined operation on the operation unit 34. Modification can be done very easily since the initial image is not an image obtained by cutting out a portion of the original image, but an image obtained merely by enlarging a predetermined area.

For example, the initial image and the whole original image can be switched by a user's operation on the indicator A1 using the operation unit 34. Moving of the initial image in the viewer window 351, changing of a display magnification of the initial image, etc. can be carried out by a user's predetermined operation using the operation unit 34.

As described above, the radiographic-image processing device 3 according to the embodiment includes the display unit 35 and the control unit 31. The control unit 31 enlarges a predetermined area including an irradiated-field area of a radiographic image (original image) and displays the enlarged predetermined area on the display unit 31 as the initial image which is the first to be displayed after radiographic imaging.

Since only an area needed for diagnosis is enlarged and displayed on the display unit 35 without cutting out the original image, even when the displayed initial image is not appropriate for diagnosis, a scope of a diagnostic image being displayed can be easily adjusted. There is no need for reading the original image again, re-specifying an area, and so on.

According to the embodiment, the control unit 31 changes the initial image displayed on the display unit 35 in accordance with a user's operation.

Therefore the initial image can be changed to a diagnostic image which meets a user's wish.

According to the embodiment, the device includes an indicator A1 which makes a user recognize that the initial image is an enlarged image obtained by enlarging a predetermined area of the original image which includes the irradiated-field area when the initial image is displayed on the display unit 35.

Therefore a user is prevented from recognizing by mistake that the initial image is the original image when the initial image is displayed.

According to the embodiment, the indicator A1 is displayed on the display unit 35 together with the initial image when the initial image is displayed on the display unit 35. The control unit 31 changes the displayed initial image in accordance with a user's operation on the indicator A1.

Therefore the indicator A1, which is a recognition section for making a user recognize that the initial image is an enlarged image, can also be used as an operation tool for changing the initial image.

According to the embodiment, the control unit 31 switches between the initial image and the whole image obtained by radiographic imaging in accordance with a user's operation.

Therefore comparison between the initial image and the whole image can be easily carried out.

According to the embodiment, the control unit 31 moves the initial image or changes the display magnification of the initial image in accordance with a user's operation.

Therefore the initial image can be easily modified to be a diagnostic image which meets a user's wish.

According to the embodiment, the interest area is the irradiated-field area in the radiographic image.

Therefore the initial image includes at least the irradiated-field area in the original image, and the generated initial image is useful for diagnosis.

According to the embodiment, the device includes the display-information storage 333 which stores many display information that define a form and a size of an image to be displayed on the display unit 35. The control unit 31 selects information from the many information stored in the display-information storage 333 on the basis of a form and a size of the irradiated-field-including area, and sets a form and a size of a predetermined area.

For example, display information corresponding to a cassette and a film which are used in the CR device is stored. Then display information corresponding to a cassette and a film which has been used when the CR device images a diagnostic target part is selected on the basis of a form and a size of the irradiated area. An image similar to an image obtained by the CR device can be displayed on the display unit 35.

In the above embodiment, the indicator A1 is explained as an example of a recognition section. However, the recognition section can have other configuration only if the recognition section can make a user recognize that the initial image is an enlarged image of a portion of the original image.

For example, the indicator A1 can be replaced by a word "initial image" displayed in the initial image. Also, the device can have a lamp, etc. which comes on when the initial image is displayed.

In the above embodiment, the indicator A1 which serves as both the recognition section and the operation tool is explained as an example. The recognition section makes a user recognize that the initial image is an enlarged image. The operation tool changes the initial image. However, it is also possible that the indicator A1 does not serve as both the recognition section and the operation tool.

In the above embodiment, it is illustrated that the interest area of a radiographic image is an irradiated-field area of radiation. However, in addition to this, the interest area of a radiographic image can be, for example, an area which a user sets at will. In this case, for example, a specific form is stored in advance, and an area having the form is defined as the interest area.

<Variation>

Figure 20:
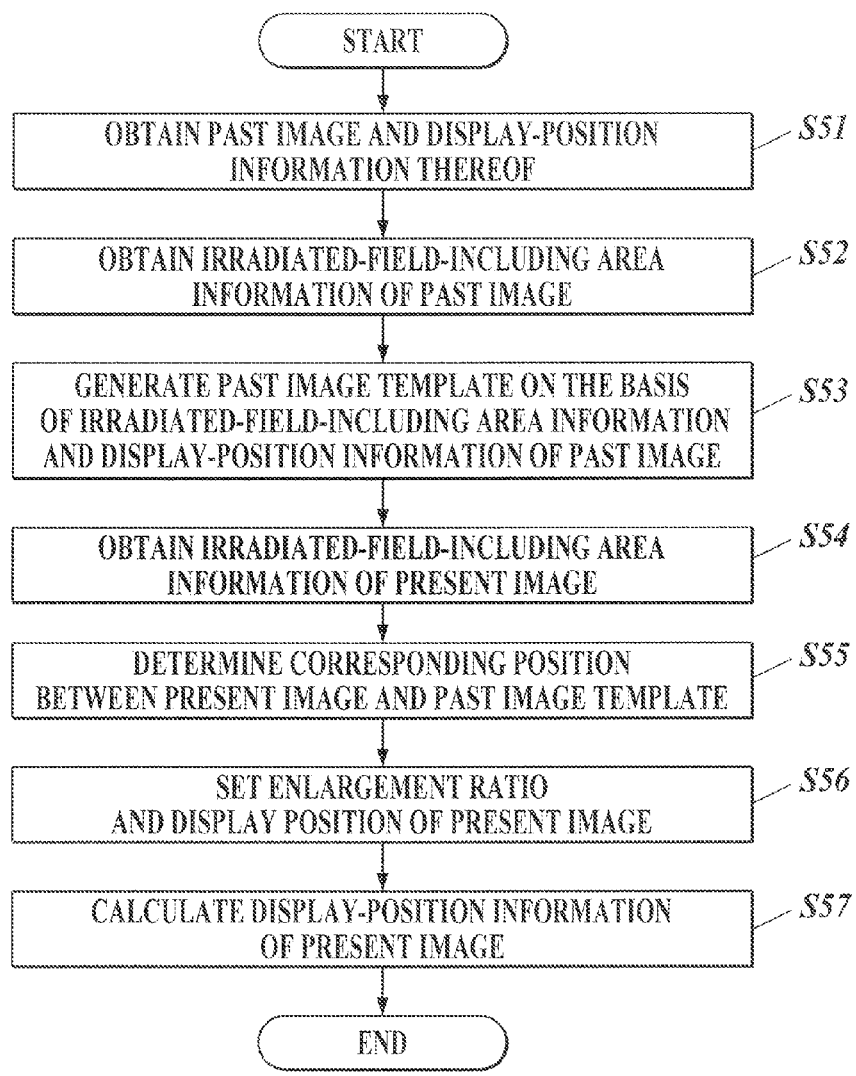
FIG. 20 shows a flowchart of a variation of the display-area setting processing in FIG. 18.

In addition to the processing shown in FIG. 18, the display-area setting processing can be, for example, the following processing shown in FIG. 20.

Such display-area setting processing is also executed by the control unit 31 in cooperation with programs stored in the storage 33.

Further, such display-area setting processing is also executed on the irradiated-field-including area which is determined in the above irradiated-field-including-area determination processing. The display-area setting processing is executed, for example, to compare a present image with a past image. The past image is an image based on image data obtained by past imaging of the same portion of the same patient, which is stored in the image database 331. The present image is an image based on image data obtained by present imaging.

First, at Step S51, the control unit 31 obtains a past image of the same patient and display-position information thereof.

The display-position information of the past image includes display-starting coordinates, display-finishing coordinates and display-center coordinates in the original image of the past image in the vertical and the horizontal directions. The display-position information was calculated in the processing shown in FIG. 18 and was stored in the storage 33 when the past image was displayed in the image-display section 351a of the viewer window 351.

Next, at Step S52, the control unit 31 obtains irradiated-field-including-area information of the past image.

The irradiated-field-including-area information of the past image was calculated in the processing shown in FIG. 17 and was stored in the storage 33 when the past image was displayed in the image-display section 351a of the viewer window 351.

Next, at Step S53, the control unit 31 generates a past image template on the basis of the irradiated-field-including-area information of the past image and the display-position information of the past image.

Next, at Step S54, the control unit 31 obtains the irradiated-field-including-area information of the present image.

Next, at Step S55, the control unit 31 compares the present image with the past image template to determine corresponding position between the present image and the past image template.

Next, at Step S56, the control unit 31 determines an enlargement ratio and a display position of the present image in accordance with the past image template.

Next, at Step S57, the control unit 31 calculates display-position information of the present image and ends the processing.

After the calculation of the display-position information, generation of an initial image of the present image is executed in the processing shown in FIG. 19, and the generated initial image is displayed together with the past image.

Figure 21:
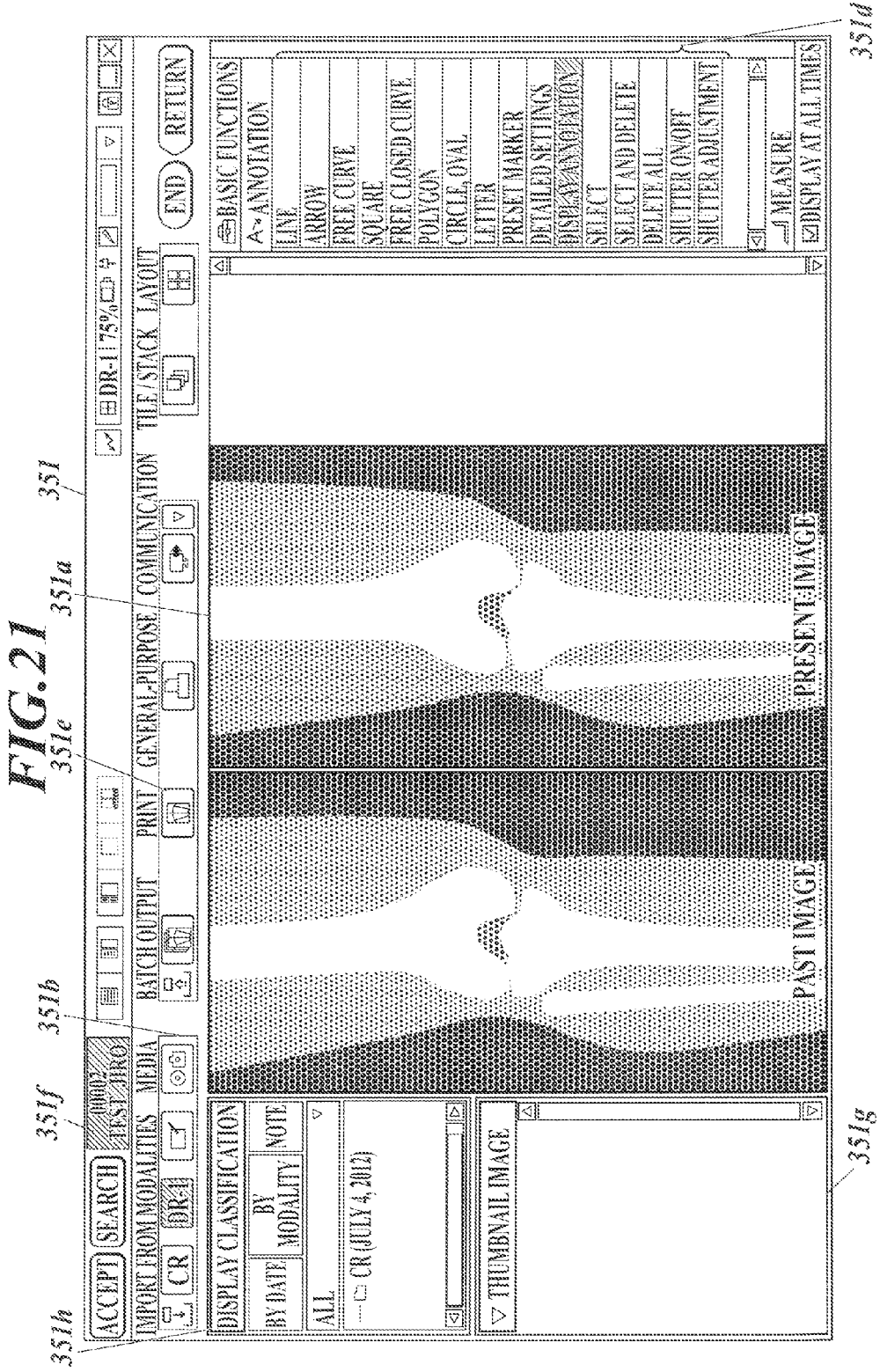
FIG. 21 shows an example of the initial image displayed in the viewer window of the display unit as a result of the processing in FIG. 20.

FIG. 21 shows an example of the past image and the present image displayed in parallel in the image-display section 351a of the viewer window 351.

As described above, the initial image is generated with reference to the past image in the display-area setting processing. Therefore diagnosis of the same part can be easily carried out.

According to one aspect of a preferable embodiment of the present invention, the radiographic-image processing device which executes image processing on radiographic image data obtained by radiographic imaging of a diagnostic target part as an imaging subject includes:

the display unit which displays a radiographic image based on the radiographic image data; and the enlargement display unit which enlarges a predetermined area including the interest area in the radiographic image and which displays the enlarged predetermined area on the display unit as the initial image which is the first to be displayed after radiographic imaging.

According to the embodiment, only an area needed for diagnosis is enlarged and displayed on the display unit without cutting out the original image. Therefore, even when the displayed initial image is not appropriate for diagnosis, a scope of a diagnostic image being displayed can be easily adjusted. There is no need for reading the original image again, re-specifying an area, and so on.

According to one aspect of a preferable embodiment of the present invention, the radiographic-image processing device further includes the display-change unit which changes the initial image displayed on the display unit in accordance with operation by a user.

According to the embodiment, the initial image can be changed to a diagnostic image which meets a user's wish.

According to one aspect of a preferable embodiment of the present invention, the radiographic-image processing device further includes the recognition section which makes a user recognize that the initial image is an enlarged image of the predetermined area including the interest area of the radiographic image when the initial image is displayed on the display unit.

According to the embodiment, a user is prevented from recognizing by mistake that the initial image is the original image when the initial image is displayed.

According to one aspect of a preferable embodiment of the present invention, the recognition section is the indicator displayed on the display unit together with the initial image when the initial image is displayed on the display unit, and the display-change unit changes the displayed initial image in accordance with operation on the indicator by a user.

According to the embodiment, the indicator A1 which is a recognition section for making a user recognize that the initial image is an enlarged image can also be used as an operation tool for changing the initial image.

According to one aspect of a preferable embodiment of the present invention, the display-change unit switches between the initial image and the whole image obtained by radiographic imaging.

According to the embodiment, comparison between the initial image and the whole image can be easily carried out.

According to one aspect of a preferable embodiment of the present invention, the display-change unit moves the initial image or changes a display magnification of the initial image.

According to the embodiment, the initial image can be easily modified to be a diagnostic image which meets a user's wish.

According to one aspect of a preferable embodiment of the present invention, the interest area is the irradiated-field area in the radiographic image.

According to the embodiment, the initial image includes at least an irradiated-field area in the radiographic image, and the generated initial image is useful for diagnosis.

According to one aspect of a preferable embodiment of the present invention, the radiographic-image processing device further includes the storage which stores the plurality of display information which defines a form and a size of an image to be displayed on the display unit, and the enlargement display unit selects display information from the plurality of display information stored in the storage on the basis of a form and a size of the interest area and sets a form and a size of the predetermined area.

According to the embodiment, for example, display information corresponding to a cassette and a film which are used in the CR device is stored. Then display information corresponding to a cassette and a film which has been used when the CR device images a diagnostic target part is selected on the basis of a form and a size of the interest area. An image similar to an image obtained by the CR device can be displayed on the display unit.

According to one aspect of a preferable embodiment of the present invention, the radiographic-image processing device further includes the past-image storage which stores past-image data obtained in past radiographic imaging, and the enlargement display unit sets a form and a size of the predetermined area on the basis of the past-image data obtained for the same diagnostic target part of the same patient, which is stored in the past-image storage.

According to the embodiment, the initial image is generated with reference to the past image. Therefore diagnosis of the same part can be easily carried out.

This U.S. patent application claims priority to Japanese patent application No. 2012-272086 filed on Dec. 13, 2012, the entire contents of which are incorporated by reference herein for correction of incorrect translation.

What is claimed is:

1. A radiographic-image processing device which executes image processing on radiographic image data obtained by radiographic imaging of a diagnostic target part as an imaging subject, the radiographic-image processing device comprising:
   a display unit which displays a radiographic image based on the radiographic image data; and
   an enlargement display unit which:
   (i) sets a rectangular area having a predetermined size on the radiographic image,
   (ii) recognizes an irradiated area as an interest area in the radiographic image based on an inside value and an outside value, the inside value being an average value of brightness signals corresponding to a radiation dose inside the rectangular area, and the outside value being a maximum value of a brightness signal corresponding to a radiation dose outside the rectangular area,
   (iii) sets an area including the recognized irradiated area as a display area, and
   (iv) displays an enlarged image of the set display area on the display unit as an initial image which is the first image to be displayed after radiographic imaging.

2. The radiographic-image processing device according to claim 1, wherein:
   the enlargement display unit calculates energy which is defined as an amount of difference between the inside value and the outside value at points on the radiographic image while moving the rectangular area which is set on the radiographic image; and
   when determining that a sum of the energy calculated at the points exceeds a predetermined threshold, the enlargement display unit sets a size and a position of the rectangular area based on the sum of the energy and determines an area included in the rectangular area as an irradiated-field-including area.

3. The radiographic-image processing device according to claim 2, wherein when determining that the sum of the energy calculated at the points is less than the predetermined threshold, the enlargement display unit changes a size of the rectangular area to set a new size of the rectangular area and calculates the energy at the points on the radiographic image while moving the rectangular area of the new size on the radiographic image.

4. The radiographic-image processing device according to claim 3, wherein when determining that the sum of the energy calculated at the points is less than the predetermined threshold and the new size of the rectangular area is not set, the enlargement display unit determines a whole area of the radiographic image as the irradiated-field-including area.

5. The radiographic-image processing device according to claim 2, wherein the enlargement display unit comprises an irradiated-field recognition unit which detects an edge of an irradiated field in the determined irradiated-field-including area to recognize the irradiated field.

6. A method of radiographic-image processing which executes image processing on radiographic image data obtained by radiographic imaging of a diagnostic target part as an imaging subject, the method comprising:
   displaying, on a display unit, a radiographic image based on the radiographic image data; and
   executing, by a processor, functions comprising:
   setting a rectangular area having a predetermined size on the radiographic image;
   recognizing an irradiated area as an interest area in the radiographic image based on an inside value and an outside value, the inside value being an average value of brightness signals corresponding to a radiation dose inside the rectangular area, and the outside value being a maximum value of a brightness signal corresponding to a radiation dose outside the rectangular area;
   setting an area including the recognized irradiated area as a display area; and
   displaying an enlarged image of the set display area on the display unit as an initial image which is the first image to be displayed after radiographic imaging.

7. A non-transitory computer-readable storage medium having a program stored thereon, the program being executable to control a radiographic-image processing device, which executes image processing on radiographic image data obtained by radiographic imaging of a diagnostic target part as an imaging subject, to perform functions comprising:

displaying, on a display unit, a radiographic image based on the radiographic image data; and executing, by a processor, functions comprising:
    setting a rectangular area having a predetermined size on the radiographic image;
    recognizing an irradiated area as an interest area in the radiographic image based on an inside value and an outside value, the inside value being an average value of brightness signals corresponding to a radiation dose inside the rectangular area, and the outside value being a maximum value of a brightness signal corresponding to a radiation dose outside the rectangular area;
    setting an area including the recognized irradiated area as a display area; and
    displaying an enlarged image of the set display area on the display unit as an initial image which is the first image to be displayed after radiographic imaging.

* * * * *